US009848605B2

(12) United States Patent
Eger, Jr. et al.

(10) Patent No.: US 9,848,605 B2
(45) Date of Patent: Dec. 26, 2017

(54) BAIT MATERIALS, PEST MONITORING DEVICES AND OTHER PEST CONTROL DEVICES THAT INCLUDE POLYURETHANE FOAM

(71) Applicant: Dow AgroSciences LLC, Indianapolis, IN (US)

(72) Inventors: Joseph Edward Eger, Jr., Tampa, FL (US); Donald E. Williams, III, Greenfield, IN (US); Sol M. Mirasol, Woodstock, GA (US); Mike P. Tolley, Indianapolis, IN (US); Joseph J. DeMark, Fayetteville, AR (US); Matthew T. Messenger, Alexandria, VA (US); Phillip J. Howard, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/840,619

(22) Filed: Mar. 15, 2013

(65) Prior Publication Data
US 2013/0276354 A1 Oct. 24, 2013

Related U.S. Application Data

(62) Division of application No. 12/583,259, filed on Aug. 18, 2009, now Pat. No. 8,454,985.

(60) Provisional application No. 61/189,379, filed on Aug. 19, 2008.

(51) Int. Cl.
| | |
|---|---|
| A01N 25/16 | (2006.01) |
| A01N 47/28 | (2006.01) |
| A01M 1/02 | (2006.01) |
| A01M 1/20 | (2006.01) |
| A01N 51/00 | (2006.01) |
| A01N 25/00 | (2006.01) |
| A01N 25/22 | (2006.01) |

(52) U.S. Cl.
CPC ............ *A01N 51/00* (2013.01); *A01M 1/026* (2013.01); *A01M 1/2011* (2013.01); *A01N 25/006* (2013.01); *A01N 25/16* (2013.01); *A01N 25/22* (2013.01)

(58) Field of Classification Search
None
See application file for complete search history.

(56) References Cited

U.S. PATENT DOCUMENTS

| | | | |
|---|---|---|---|
| 3,256,218 A * | 6/1966 | Knox | B29B 7/90 264/45.3 |
| 3,318,769 A | 5/1967 | Folckemer et al. | |
| 3,564,750 A | 2/1971 | Burgess | |
| 3,778,805 A | 12/1973 | Gould | |
| 3,836,842 A | 9/1974 | Zimmermann et al. | |
| 4,074,456 A | 2/1978 | Tidwell | |
| 4,105,971 A | 8/1978 | Nevalainen | |
| 4,127,110 A | 11/1978 | Bullara | |
| 4,136,338 A | 1/1979 | Antenore | |
| 4,265,252 A | 5/1981 | Chubbuck et al. | |
| 4,366,644 A | 1/1983 | Lawrence | |
| 4,387,529 A | 6/1983 | Hedstrom | |
| 4,455,441 A | 6/1984 | Prestwich | |
| 4,472,904 A | 9/1984 | Wasielewski | |
| 4,631,231 A | 12/1986 | Stendel et al. | |
| 4,653,221 A | 3/1987 | Pratscher | |
| 4,688,026 A | 8/1987 | Scribner et al. | |
| 4,737,770 A | 4/1988 | Brunius et al. | |
| 4,737,789 A | 4/1988 | Nysen | |
| 4,843,752 A | 7/1989 | Munemasa et al. | |
| 4,862,145 A | 8/1989 | Meehan et al. | |
| 4,927,863 A | 5/1990 | Bartlett et al. | |

(Continued)

FOREIGN PATENT DOCUMENTS

| | | |
|---|---|---|
| CA | 355888 | 2/1936 |
| EP | 0281342 A1 | 9/1988 |
| EP | 1563730 A1 | 8/2005 |
| FR | 1000498 | 2/1952 |
| GB | 117916 | 8/1917 |

(Continued)

OTHER PUBLICATIONS

XP-002167430, Jurgens et al., "Development and Evaluation of an Inexpensive Sensor System for Use in Measuring Relative Finger Positions," vol. 19, Medical Engineering & Physics, Elsevier Science Ltd., Oxford, Englang, Jan. 1997. (Abstract only).

(Continued)

*Primary Examiner* — Abigail Vanhorn
(74) *Attorney, Agent, or Firm* — Carl D. Corvin

(57) ABSTRACT

A termite bait includes a plurality of cellulosic food material pieces palatable to termites embedded within a water resistant polyurethane foam matrix. Another termite bait includes a plurality of cellulosic food material pieces embedded within a water-absorbent polyurethane foam matrix. Yet another termite bait includes at least one cellulosic food material piece encapsulated within a water resistant polyurethane foam coating. Such termite baits can be used alone or in a monitoring device or other termite control device. Another termite control device includes a container, a cellulosic food material within the container and a water resistant polyurethane foam positioned to separate the food material from its environment. The container can contain a termite bait as described above or can include a chamber containing a cellulosic food material and at least one pocket containing a polyurethane foam barrier to reduce intrusion of water through the pocket to the food material.

21 Claims, 15 Drawing Sheets

(56) References Cited

U.S. PATENT DOCUMENTS

| | | |
|---|---|---|
| 4,951,057 A | 8/1990 | Nagel |
| 4,961,283 A | 10/1990 | Forbes |
| 4,988,510 A | 1/1991 | Brenner et al. |
| 5,024,832 A | 6/1991 | Omata et al. |
| 5,042,194 A | 8/1991 | Cohen |
| 5,079,238 A | 1/1992 | Van Horn |
| 5,116,414 A | 5/1992 | Burton et al. |
| 5,134,892 A | 8/1992 | Wilson et al. |
| 5,209,233 A | 5/1993 | Holland et al. |
| 5,237,310 A | 8/1993 | Smith |
| 5,285,688 A | 2/1994 | Robbins et al. |
| 5,329,726 A | 7/1994 | Thorne et al. |
| 5,428,345 A | 6/1995 | Bruno |
| 5,429,735 A | 7/1995 | Johnson et al. |
| 5,528,222 A | 6/1996 | Moskowitz et al. |
| 5,564,222 A | 10/1996 | Brody |
| 5,571,967 A | 11/1996 | Tanaka et al. |
| 5,575,105 A | 11/1996 | Otomo |
| 5,592,774 A | 1/1997 | Galyon |
| 5,648,758 A | 7/1997 | Tweadey, II et al. |
| 5,661,651 A | 8/1997 | Geschke et al. |
| 5,739,514 A | 4/1998 | Uchida |
| 5,764,138 A | 6/1998 | Lowe |
| 5,801,194 A * | 9/1998 | Voris et al. ............... 514/531 |
| 5,815,090 A | 9/1998 | Su |
| 5,864,241 A | 1/1999 | Schreck et al. |
| 5,866,269 A | 2/1999 | Dalebroux et al. |
| 5,876,577 A | 3/1999 | McAleer et al. |
| 5,877,422 A | 3/1999 | Otomo |
| 5,892,444 A | 4/1999 | Wittmer et al. |
| 5,894,818 A | 4/1999 | Betzen |
| 5,910,776 A | 6/1999 | Black |
| 5,937,571 A | 8/1999 | Megargle et al. |
| 5,950,356 A | 9/1999 | Nimocks |
| 5,974,344 A | 10/1999 | Shoemaker, II |
| 5,974,726 A | 11/1999 | Creeger et al. |
| 5,986,570 A | 11/1999 | Black et al. |
| 5,997,784 A | 12/1999 | Karnoski |
| 6,016,625 A | 1/2000 | Bishoff et al. |
| 6,025,725 A | 2/2000 | Gershenfeld et al. |
| 6,060,076 A | 5/2000 | Voris et al. |
| 6,099,850 A | 8/2000 | Voris et al. |
| 6,100,805 A | 8/2000 | Lake |
| 6,111,520 A | 8/2000 | Allen et al. |
| 6,130,602 A | 10/2000 | O'Toole et al. |
| 6,150,944 A | 11/2000 | Martin et al. |
| 6,178,834 B1 | 1/2001 | Cates |
| 6,187,328 B1 | 2/2001 | Ballard et al. |
| 6,243,014 B1 | 6/2001 | Lake et al. |
| 6,255,959 B1 | 7/2001 | Lake et al. |
| 6,281,799 B1 | 8/2001 | Lake et al. |
| 6,304,185 B1 | 10/2001 | Tuttle et al. |
| 6,313,748 B1 | 11/2001 | Lake |
| 6,319,511 B1 | 11/2001 | Van Voris et al. |
| 6,337,079 B1 | 1/2002 | Maindron |
| 6,339,897 B1 | 1/2002 | Hayes et al. |
| 6,370,812 B1 | 4/2002 | Burns et al. |
| 6,397,516 B1 | 6/2002 | Su |
| 6,404,210 B1 | 6/2002 | Su |
| 6,416,752 B1 | 7/2002 | Richardson et al. |
| 6,478,440 B1 | 11/2002 | Jaworski et al. |
| 6,515,591 B2 | 2/2003 | Lake et al. |
| 6,537,407 B1 | 3/2003 | Law et al. |
| 6,581,325 B2 | 6/2003 | Gordon |
| 6,581,625 B1 | 6/2003 | Arai et al. |
| 6,585,991 B1 * | 7/2003 | Rojas et al. ............... 424/410 |
| 6,615,535 B2 | 9/2003 | Snell et al. |
| 6,630,887 B2 | 10/2003 | Lake et al. |
| 6,668,483 B1 | 12/2003 | Trivisani et al. |
| 6,681,518 B2 | 1/2004 | Aesch, Jr. et al. |
| 6,724,312 B1 | 4/2004 | Barber et al. |
| 6,803,051 B1 | 10/2004 | Voris et al. |
| 6,852,328 B1 | 2/2005 | Voris et al. |
| 6,857,223 B2 | 2/2005 | Su |
| 6,875,440 B2 | 4/2005 | Aki et al. |
| 6,881,367 B1 | 4/2005 | Baker |
| 6,914,529 B2 | 7/2005 | Barber et al. |
| 6,937,156 B2 | 8/2005 | Gardner, Jr. et al. |
| 7,163,974 B2 | 1/2007 | Manning et al. |
| 7,169,403 B2 | 1/2007 | Su |
| 7,212,112 B2 | 5/2007 | Barber et |
| 7,212,129 B2 | 5/2007 | Barber et al. |
| 7,262,702 B2 | 8/2007 | Barber et al. |
| 7,335,374 B2 | 2/2008 | Voris et al. |
| 7,348,890 B2 | 3/2008 | Barber et al. |
| 8,001,622 B1 * | 8/2011 | Culley ............... A42B 3/127 2/267 |
| 8,454,985 B2 | 6/2013 | Eger, Jr. et al. |
| 2001/0009399 A1 | 7/2001 | Barber et al. |
| 2001/0054962 A1 | 12/2001 | Barber et al. |
| 2002/0018884 A1 * | 2/2002 | Thomson ............... 428/306.6 |
| 2002/0101352 A1 | 8/2002 | Barber et al. |
| 2002/0192259 A1 | 12/2002 | Voris et al. |
| 2003/0049293 A1 | 3/2003 | Jobic |
| 2003/0152605 A1 | 8/2003 | Martin et al. |
| 2003/0160699 A1 | 8/2003 | Trompen |
| 2004/0079025 A1 | 4/2004 | Snell et al. |
| 2005/0091911 A1 | 5/2005 | Matts et al. |
| 2005/0233138 A1 | 10/2005 | Jobic |
| 2006/0117645 A1 | 6/2006 | Cink et al. |
| 2006/0201053 A1 | 9/2006 | Voris et al. |
| 2006/0254123 A1 | 11/2006 | Su |
| 2007/0044372 A1 | 3/2007 | Lang et al. |
| 2007/0120690 A1 | 5/2007 | Barber et al. |
| 2008/0055094 A1 | 3/2008 | Barber et al. |
| 2008/0081030 A1 | 4/2008 | DeMark et al. |
| 2008/0083746 A1 | 4/2008 | Lucas et al. |
| 2008/0138129 A1 | 6/2008 | Lucas et al. |
| 2008/0187565 A1 | 8/2008 | Hill et al. |
| 2009/0188155 A1 | 7/2009 | Tolley et al. |
| 2013/0276352 A1 | 10/2013 | Eger, Jr. et al. |
| 2013/0276353 A1 | 10/2013 | Eger, Jr. et al. |

FOREIGN PATENT DOCUMENTS

| | | |
|---|---|---|
| GB | 590826 | 7/1947 |
| GB | 1040553 | 9/1966 |
| GB | 1513190 | 6/1978 |
| JP | 52-38005 | 3/1977 |
| JP | 7-43460 | 2/1995 |
| JP | 9-26320 | 1/1997 |
| JP | 9-98701 | 4/1997 |
| JP | 10-56935 | 3/1998 |
| JP | 10-84834 | 4/1998 |
| JP | 10-105861 | 4/1998 |
| JP | 11-239440 | 9/1999 |
| WO | WO 93-23998 | 12/1993 |
| WO | WO 98/21961 | 5/1998 |
| WO | WO 98/46071 | 10/1998 |
| WO | WO 99/41983 | 8/1999 |
| WO | WO 00/62610 | 10/2000 |
| WO | WO 00173243 | 12/2000 |
| WO | WO 01/06851 | 2/2001 |
| WO | WO 02/26033 | 4/2002 |
| WO | WO 02/43487 | 6/2002 |
| WO | WO 03/013237 | 2/2003 |
| WO | WO 03/067977 | 8/2003 |
| WO | WO 03/079779 | 10/2003 |
| WO | WO 03/082000 | 10/2003 |
| WO | WO 03/082002 | 10/2003 |
| WO | WO 2005/092029 | 10/2005 |
| WO | WO 2007/014344 | 2/2007 |
| WO | WO 2007/106726 A2 | 9/2007 |
| WO | WO 2008/063939 A2 | 5/2008 |
| WO | WO 2008/079384 | 7/2008 |
| ZA | 847774 | 10/1984 |

OTHER PUBLICATIONS

XP-002167431, Shin'nosuke et al., "Electrical2 Properties of Carbon Black-Graftpolymers Crosslinked with Peroxide-Divinyl Monomer System," vol. 25, J Soc Meter Sci Jpn, Oct. 1976. (Abstract only).

(56) References Cited

OTHER PUBLICATIONS

XP-002167432, Rosenbaum et al., "A Survey of Some Secondary Thermometers for Possible3 Applications At Very Low Temperatures," vol. 41, Rev Sci Instrum, Jan. 1970 (Abstract only).
Sentricon Colony Elimination System; Dow AgroSciences; Mar. 26, 19994.
Phillipp et al., "Charge Transfer Sensing" Copyright © 1999.
Passive RFID Device with Sensor Input; MCRF202; Microchip Technology Inc.; Copyright © 1999.
DS2405 Adressable Switch, Dallas Semiconductor, Jul. 2002.
Willeltner et al., "Possibillities and problems related to Incorporation of fungicides and insecticides into primers and lacquers used for treatment of wood," Inst. Holzblo. Holzschultz, Bundesforschungsanst. Forst-Holzwirtsch. Reinbek, Hamburg, Fed. Rep. Ger. Fette, Selfan, Anstrichnittel (1974), 76(12). 533-8.
Disclosed anonymously. Extruded Thermoplastic and Cellulose Materials Acceptable to Termites as Monitors or Bait. Prior Art Database, www.ip.com, May 3, 2005.
SciFinder Search Report; Sep. 14, 2003.
Su, "Hermetically Sealed Baits for Subterranean Termites (*Isoptera: rhinotermitidae*)", Journal of Economic Entomology 100 (2): 475-482. 2007.

\* cited by examiner

BAIT MATERIALS, PEST MONITORING DEVICES AND OTHER PEST CONTROL DEVICES THAT INCLUDE POLYURETHANE FOAM

CROSS-REFERENCE TO RELATED APPLICATIONS

The present application is a divisional of U.S. patent application Ser. No. 12/583,259 filed on 18 Aug. 2009, which claims the benefit of U.S. Provisional Patent Application No. 61/189,379 filed on 19 Aug. 2008, each of which is hereby incorporated by reference in its entirety.

BACKGROUND

The present application relates to pest control, and more particularly, relates to techniques for using a polyurethane foam in a bait material and/or in a monitoring device or other termite control device.

The removal of pests from areas occupied by humans, livestock, and crops has long been a challenge. Pests of frequent concern include various types of insects and rodents. Subterranean termites are a particularly troublesome type of pest with the potential to cause severe damage to wooden structures. Various schemes have been proposed to eliminate termites and certain other harmful pests of both the insect and noninsect variety. In one approach, pest control relies on the blanket application of chemical pesticides in the area to be protected. However, this approach is becoming less desirable than targeted pesticide delivery, which can be more efficient and environmentally friendly.

Recently, advances have been made to provide for the targeted delivery of pesticide chemicals. U.S. Pat. No. 5,815,090 to Su is one example. Another example directed to termite control is the SENTRICON TERMITE COLONY ELIMINATION SYSTEM™ of Dow AgroSciences LLC that has a business address of 9330 Zionsville Road, Indianapolis, Ind. In this system, a number of units each having a termite edible material, are placed in the ground about a dwelling to be protected. The units are inspected routinely by a pest control service for the presence of termites, and inspection data is recorded with reference to a unique barcode label associated with each unit. If termites are found in a given unit, a bait is installed that contains a slow-acting pesticide intended to be carried back to the termite nest to eradicate the colony. U.S. Pat. Nos. 6,724,312; 7,212,112; and 7,212,129; and U.S. Patent Application Publication Nos. 2001/0033230 and 2001/0054962 provide further examples.

In certain instances, the bait in an in-ground pest control device, such as a monitoring device or a pesticide delivery device, degrades with prolonged exposure to moisture, which can undermine its appeal to targeted pests, and sometimes results in improper operation of associated sensors (if present). Frequently, it is desirable to maintain the palatability of the bait in a pest control device over a longer period of time and/or better control moisture intrusion. In other instances, the bait in an above-ground pest control devices loses its appeal to target pests when it becomes dried, which can undermine its efficacy to eradicate a termite colony. In addition, currently available above-ground pest control devices utilize preferred texture cellulose (PTC) bait materials, which are contained in a polyethylene bag that is cut open for termite entry. When termites feed on the PTC in the bag, they also typically impart significant damage to the bag so that the PTC spills from the above-ground station when it is opened, causing a significant mess and inconvenience for users. Thus, there is a demand for further contributions in this area of technology.

SUMMARY

One embodiment of the present application is a unique technique for pest control. Other embodiments include unique apparatus, systems, methods, materials and devices to protect bait in an in-ground pest control device, such as a monitoring device or a pesticide delivery device, from moisture intrusion or the like. Still other embodiments include unique apparatus, systems, methods, materials and devices to protect an above-ground bait from becoming desiccated. Further embodiments, forms, features and aspects shall become apparent from the following description and drawings.

DETAILED DESCRIPTION OF REPRESENTATIVE EMBODIMENTS

Figure 1:
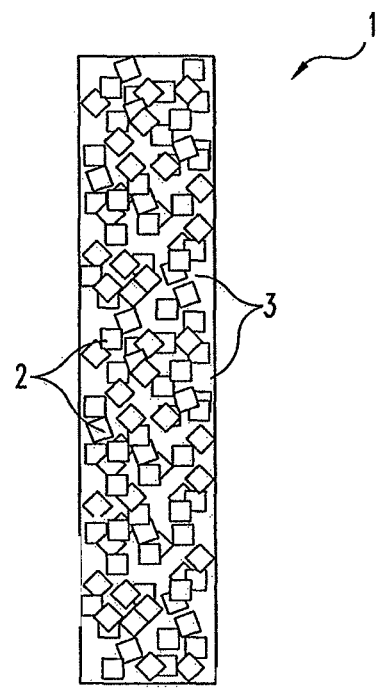
FIG. 1 is a diagrammatic view of a composite bait material according to one embodiment of the present application.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present application relates to the inclusion of a polyurethane foam in a bait material or in a termite control device, such as, for example a monitoring device or pesticide delivery device. The terms "bait" and "bait material" are used interchangeably herein to refer to a material that is attractive to termites, including, for example, a material that is edible by the termites, a material that includes chemical or biochemical agents that attract termites, and/or a material that is otherwise effective to attract termites, whether or not the material includes a pesticide and whether the material is used in an monitoring device, a pesticide delivery device or other termite control device. The polyurethane foam can provide a variety of functions when included in a bait material or in a termite control device. For example, in one embodiment a closed-cell or properly selected open-cell polyurethane foam can be used to provide a moisture barrier protecting a cellulosic food material in a bait material or in an in-ground pest control device, thereby maintaining palatability of the bait over an extended period of time. In another embodiment, an open-cell polyurethane foam can be used to provide a structural matrix for a cellulosic food material to hold moisture in contact with the food material in an above-ground pest control device to make the food material more attractive to termites. The polyurethane foam can also operate to hold a bait material together to prevent crumbling and spilling of the bait, such as commonly occurs when an above-ground station containing a conventional bait material is opened.

In one aspect, the application provides a moisture-resistant composite bait material that is operable to be consumed or displaced by one or more species of termites. With reference to the embodiment depicted in FIG. 1, composite bait material 1 includes a plurality of cellulosic food material pieces 2 that are palatable to the termite species, embedded within a termite-edible or termite-displaceable polyurethane foam matrix 3. In some uses of a termite bait, it is desirable to attract termites to a bait material without delivering a pesticide. One example is a bait intended for use in a monitoring device to monitor an area for the presence of termites. Such a bait material can be observed periodically to determine whether termites are actively feeding in the area. Multiple examples of the use of a composite bait material in a monitoring device are described further hereinbelow. In other uses of a termite bait, it is desirable to attract termites and to deliver a pesticide to the termites attracted to the bait. A bait used in this manner can include a pesticide in the bait material. The term "pesticide" is used herein to refer to a compound that is toxic to at least one target species of termites. In an embodiment that includes a pesticide, the pesticide retains its bioactivity as it resides within composite bait material 1, and produces a desired result after the material is ingested by or otherwise comes into contact with termites as composite bait material 1 is consumed or displaced by the termites.

In one embodiment, foam matrix 3 is composed of a closed-cell polyurethane foam. In this embodiment, foam matrix 3 provides a water resistant barrier surrounding at least one, and preferably most or all, of cellulosic food material pieces 2. In certain embodiments, foam matrix 3 separately encapsulates, or compartmentalizes, some or all of the cellulosic food material pieces, which increases the operational life of bait material pieces 2, even when bait material 1 is exposed to moisture, and even after some of matrix 3 is consumed by termites or otherwise breached. In such embodiments, after a portion of the bait matrix is consumed or breached, the remaining portions of foam matrix 3 continue to functionally protect the remainder of the cellulosic food material pieces that remain encapsulated by foam matrix 3. The bait material of this embodiment is useful in situations where it is desirable for the bait to withstand exposure to moist conditions without becoming fouled for an extended period of time.

In another embodiment, foam matrix 3 is composed of an open-cell polyurethane foam, and operates to hold moisture in contact with food material pieces 2. A bait material of this embodiment is useful in situations where it is desirable for food material pieces 2 to be kept in a moistened state for an extended period of time, such as, for example, for use in an above-ground termite control station, as will be described further hereinbelow.

In one embodiment, cellulosic food material pieces 2 are selected based upon known or measured attractability for termites. The cellulosic food material therefore attracts members of a termite colony and would be expected to be consumed or displaced by the termites. In one embodiment, the cellulosic food material pieces are cellulose briquettes, such as, for example, RECRUIT IV™ cellulose briquettes, which are commercially available from Dow Agrosciences LLC (Indianapolis, Ind.). In other embodiments, other cellulose briquettes or other cellulose-containing materials, with or without a pesticide contained therein, can be used. In one embodiment, the food material is composed in whole or in part of an edible plastic material, which can include cellulose therein (referred to as a "cellulose plus plastic" material). For example, cellulosic food material pieces 2 can be composed of a material including a thermoplastic polymer, such as, for example, a material made as described in the commonly-owned U.S. Patent Application Publication No. 2008/0187565, which is hereby incorporated by reference herein in its entirety. For example, cellulosic food material pieces 2 can be made by molding, extruding or otherwise processing a termite-edible thermoplastic material or a mixture of a thermoplastic material and a pest food material, with or without a pesticide included therein. A material including a thermoplastic polymer can be molded into predetermined shapes and sizes for use as food material pieces 2, or can optionally be formed into a larger workpiece from which food material pieces 2 having desired sizes and shapes can be obtained, for example, by cutting, breaking, grinding, machining or otherwise processing the workpiece into food material pieces. The present application also contemplates, particularly in connection with embodiments in which food material pieces 2 are provided by breaking or grinding a larger workpiece, that the process can also include one or more screening steps to separate particles and/or pieces into desired size fractions.

In another embodiment, the food material is a purified cellulose, such as, for example, alpha cellulose, beta cellulose or gamma cellulose. One suitable example is preferred texture cellulose (PTC). Cellulosic food material pieces having a wide variety of sizes and shapes can be made from cellulose particles, for example, by compacting the cellulose and breaking the compacted material into prills. In addition, pre-formed prills of cellulose are available commercially, and can be obtained from International Fiber Corporation (North Tonawanda, N.Y.). In other embodiments, the food material is wood or a derivative of wood, such as, for example, wood chips, wood fibers, sawdust, cardboard, paper or other material that is palatable to a target wood-destroying species. Such materials can be provided in a wide variety of sizes and shapes. Other cellulosic food materials that can be employed include microcrystalline cellulose, examples of which are provided in U.S. Pat. No. 6,416,752, which is incorporated herein by reference, and modified polymeric cellulose based materials such as, for example, METHOCEL® or ETHOCEL®, which are available commercially from The Dow Chemical Company (Midland, Mich.). The present application also contemplates that a variety of different types of food material can be included in the composite bait material.

Polyurethane foam matrix 3 is displaced or consumed by termites, and therefore does not prevent termites from tunneling to and feeding on the cellulosic food material pieces. Polyurethane foam matrix 3 can be made to have a wide variety of properties for producing composite bait materials having a wide variety of physical features. For example, polyurethane foam matrix 3 can be made in an open-cell or closed-cell configuration, can be made to exhibit varying degrees of rigidity/flexibility, and can be made to have a wide variety of densities. It can also be formed to incorporate one or more termite feeding enhancer, such as, for example, a cellulose in a powder form, a sugar or a chemical or biochemical termite attractant into the polyurethane foam to increase termite penetration, as discussed further hereinbelow.

In one manner of making a composite bait material, a plurality of pieces of a cellulosic food material are provided in a bait enclosure so that the bait enclosure and the plurality of cellulosic food material pieces define a void space therebetween. The bait enclosure can be, for example, a bait tube configured for placement in a bait station, as described in further detail hereinbelow, or can be a mold that is used temporarily for the purpose of making a composite bait material article of a given shape. A mold would be used, for example, to make a bait material that is desired to be used as a stand-alone bait material or to be later inserted into a bait container. In an embodiment for use as a stand-alone bait material, polyurethane foam matrix 3 provides sufficient strength and structural integrity for a desired end use of composite bait material 1, even in the absence of a bait container.

With the pieces of a cellulosic food material positioned in the bait enclosure, an uncured mixture of polyurethane foam precursors is then introduced into the bait enclosure such that the mixture enters at least some of the void space. The mixture is then allowed to cure to provide a polyurethane foam barrier surrounding at least one, and preferably most or all, of the plurality of cellulosic food material pieces. The uncured mixture of polyurethane foam precursors includes at least one diisocyanate or polyisocyanate (referred to collectively herein as "isocyanate molecules" or "isocyanates") and at least one polyol. Polyurethane foam matrix 3 is produced via reaction of isocyanate molecules and polyol molecules. While the reaction is exothermic, the curing process does not produce an excessive amount of heat that would damage the cellulosic food material pieces, pesticides, or other materials present in the composite material. In certain preferred embodiments, the curing process, during which the precursors react to form polyurethane foam, is accompanied by expansion of the mixture as it undergoes the curing reaction. In one embodiment, for example, the mixture of polyurethane precursors includes water, which reacts with isocyanates in the mixture to produce carbon dioxide, which expands the mixture and causes the mixture to move into additional portions of the void space. A polyurethane foam that expands by the generation of carbon dioxide is referred to herein as a "self-expanding foam." One or more vent holes can be provided in the bait enclosure, if desired, to allow for release of pressure within the bait enclosure as the mixture cures, and for excess material to escape the bait enclosure as it expands during curing.

Many different kinds of polyurethane materials can be produced from a few types of isocyanates and a range of polyols with different functionality and molecular weights. Some of the diversity of polyurethane foam materials depends on whether the polyols used to make a given polyurethane foam are based on polyether or polyesters, both of which are contemplated by the present application. In one embodiment, foam matrix 3 is made from a mixture of precursor ingredients that includes at least one polyether polyol. Polyether polyols include the repeating ether linkage —R—O—R— and have two or more hydroxyl groups as terminal functional groups. Polyether polyols are produced by the oxyalkylation of discrete polyfunctional initiators (also referred to as "starters"). They are manufactured commercially by the catalyzed addition of epoxies (cyclic ethers), such as, for example, propylene oxide, ethylene oxide or butylene oxide, to active hydrogen-containing initiator compounds, such as, for example, glycerin, trimethylolpropane, pentaerythritol, sucrose, sorbitol, water, bisphenol A, ethylenediamine, toluenediamine, ethylene glycol, and propylene glycol; thus, a wide variety of compositions of varying structures, chain lengths and molecular weights is possible. The physical properties of the polyols are influenced primarily by the functionality of the initiator molecules and by the type and quantity of alkylene oxide and hydroxyl groups present in the polyol. In general, the functionality of the polyether is carried over from the functionality of the initiator used. By selecting a certain oxide (or oxides), initiator, and reaction conditions and catalysts, it is possible to synthesize polyether polyols that range from low-molecular-weight polyglycols to high-molecular-weight resins. Since polyether polyols include repeating alkylene oxide units, they are often referred to as polyalkylene glycols or polyglycols. The terms "polyglycol" and "polyether polyol" are used interchangeably. Polyols of interest for polyurethane foams generally are based on initiators with a functionality (active hydrogen content) of three or higher. Flexible foams typically employ tri-functional polyols, while higher-functional polyols are typically used in the production of rigid foams. The following table lists a variety of commercially available polyether polyol types that can be used to make a polyurethane foam in accordance with the present application, plus initiators and cyclic ethers (oxides) that can be used in their preparation:

cially. It is well within the purview of a person of ordinary skill in the art to select a suitable catalyst for a given polyurethane foam formulation. In one embodiment, the catalyst is a metal complex, a metal salt or a tertiary amine. Examples of metal complexes that can be used include,

TABLE 1

Selected Commercial Polyether Polyols and Reactants

| Product | Initiator | Cyclic Ether |
|---|---|---|
| Difunctional | | |
| Polypropylene Glycol (PPG) | Water or propylene glycol | Propylene oxide |
| Polyethylene Glycol (PEG) | Water or ethylene glycol | Ethylene oxide |
| Polyoxypropylene-Polyoxy-ethylene Block Copolymer | Water, propylene glycol or glycerin * | Propylene oxide and ethylene oxide |
| Polytetramethylene Ether Glycol (PTMEG) | Water | Tetrahydrofuran |
| Aromatic Diol | Bisphenol A | Propylene oxide or ethylene oxide |
| Amine Adducts | Primary monoamines ** | Propylene oxide or ethylene oxide |
| Trifunctional | | |
| Glycerin Adduct | Glycerin | Propylene oxide |
| Trimethylolpropane Adduct | Trimethylolpropane | Propylene oxide |
| Trimethylolethane Adduct | Trimethylolethane | Propylene oxide |
| Tetrafunctional | | |
| Pentaerythritol Adduct | Pentaerythritol | Propylene oxide |
| Ethylenediamine Adduct | Ethylenediamine | Propylene oxide |
| Phenolic Resin Adduct | Phenolic resin | Propylene oxide |
| Methyl Glucoside Adduct | Methyl Glucoside | Propylene oxide |
| Pentafunctional | | |
| Diethylenetriamine Adduct | Diethylenetriamine | Propylene oxide |
| Hexafunctional | | |
| Sorbitol Adducts | Sorbitol | Propylene oxide or ethylene oxide |
| Octafunctional | | |
| Sucrose Adducts | Sucrose | Propylene oxide |

* Other compounds, including trimethylolpropane, trimethylolethane, pentaerythritol, ethylenediamine, sorbitol and sucrose, can also be used as initiators for block copolymers based on propylene oxide and ethylene oxide.
** Primary monoamines include aniline, cyclohexylamine and others. The compositions made from these amines and oxides are principally surface-active agents.

The isocyanate used to make the polyurethane foam can be a diisocyanate, which includes two isocyanate groups, or a polyisocyanate, which includes three or more isocyanate groups, and may include several isocyanate groups. Suitable diisocyanates for use in the present application include, for example, methylene bis(phenyl isocyanate) (also referred to as "methylene diphenyl diisocyanate" or MDI), toluene diisocyanate (TDI), hexamethylene diisocyanate (HDI), naphthalene diisocyanate (NDI), isophorone diisocyanate (IPDI), methylene bis-cyclohexylisocyanate (HMDI) (hydrogenated MDI), and isophorone diisocyanate (IPDI). Examples of suitable polyisocyanates include HDI biuret and HDI isocyanurate. The isocyanate group reacts with the hydroxyl functional group to form a urethane linkage. If a diisocyanate is reacted with a compound containing two or more hydroxyl groups (a polyol), long polymer chains are formed, producing polyurethanes.

In addition to the polyol and isocyanate components, the mixture of polyurethane foam precursors also optionally includes a catalyst. While some polyols have catalytic activity, and thus a separate catalyst can be omitted, a catalyst will typically be included to increase the rate of the curing reaction. A wide variety of polyurethane catalysts are described in the literature, and many are available commerwithout limitation, complexes of tin, zinc, bismuth and/or lead. Examples of metal salts that can be used include, without limitation, sodium salts and/or potassium salts. The catalyst is operable in various formulations for the purpose of blowing (i.e., catalyzing the reaction of water and isocyanate to produce carbon dioxide), gelling (i.e., catalyzing the reaction of the polyol and isocyanate to produce a polyurethane polymer) and/or isocyanate trimerization. Metal complex catalysts and metal salt catalysts, for example, effectively catalyze gelling and isocyanate trimerization reactions. Tertiary amine catalysts are effective for catalyzing blowing, gelling and isocyanate trimerization reactions. In one embodiment, the catalyst is bis(dimethylaminopropyl) methylamine, which is available commercially as the product POLYCAT 77®.

The mixture of polyurethane foam precursors can also optionally include a wide variety of additional ingredients, such as, for example and without limitation, a surfactant, a flame retardant, a blowing agent, a low molecular weight multifunctional alcohol, such as, for example, diethyl glycol, an inorganic filler, a pigment or dye, an antioxidant, a plasticizer, such as, for example, a phthalate ester, and/or an antimicrobial additive. Examples of these optional additives are well known in the art and are available commercially.

As stated above, in one embodiment the mixture of polyurethane precursors includes water in an amount effective to react with the isocyanate component to produce carbon dioxide during the curing reaction. The amount of water included in the mixture can be adjusted to modify the density of the resulting polyurethane foam. As will be appreciated by a person of ordinary skill in the art, the amount of carbon dioxide produced is directly related to the amount of water in the mixture (as long as sufficient isocyanate is present for the water to fully react), and the amount of carbon dioxide produced is inversely related to the density of the resulting polyurethane foam. In addition, the final density of polyurethane foam depends not only on the amount of carbon dioxide produced during the blowing reaction, but also upon how much the foam is confined during expansion. After the liquid mixture of polyurethane foam precursors is added to the bait container or mold and the curing reaction begins, the foam expands to fill the void space. As the foam expands, it becomes more viscous. Because the foam is at least partially confined in the mold or bait container during foam formation, its expansion is partially restrained, which causes increased pressure on the curing material, reducing the volume of space occupied by the carbon dioxide, and resulting in a final density that is greater than if the foam were allowed to expand without restraint. Therefore, by controlling the amount of blowing agent present and by controlling the degree to which expansion is restrained, the density of the final product can be controlled. In one embodiment, the polyurethane foam in the composite bait material has a density of from about 2 to about 6 pounds per cubic foot. In another embodiment, the polyurethane foam in the composite bait material has a density of from about 3 to about 5 pounds per cubic foot. In another embodiment, the polyurethane foam in the composite bait material has a density of from about 3.5 to about 4.5 pounds per cubic foot. In yet another embodiment, the polyurethane foam has a density of about 4 pounds per cubic foot. When making a composite bait material by curing the polyurethane foam in a bait tube sized to fit in a SENTRICON TERMITE COLONY ELIMINATION SYSTEM® bait station, or in a mold or bait enclosure of similar dimensions, it has been found that a mixture of polyurethane foam precursors that would produce a foam having a density of about 2 pounds per cubic foot in the absence of expansion resistance will produce a foam having a density of about 4 pounds per cubic foot as a result of the pressure in the bait tube resulting from resistance during flow of the curing foam through the void space. While the effect of pressure on final density is expected to differ for mixtures having different formulations of ingredients, it is within the purview of a person of ordinary skill in the art, in view of the descriptions herein and without undue experimentation, to select formulations and pressures to produce a polyurethane foam having a desired density.

The present application also contemplates that polyurethane foams can be made using alternative gaseous ingredients as blowing agents. For example, a mixture of polyurethane foam precursors can be provided in a delivery system that includes a gaseous blowing agent, such as for example, the GREAT STUFF™ polyurethane foam system that is commercially available from The Dow Chemical Company. In embodiments in which alternative gaseous ingredients are provided, the generation of carbon dioxide during the curing reaction is unnecessary, and water can be omitted from the mixture, or included in a lesser amount.

As will be appreciated by a person of ordinary skill in the art, it is important to prevent mixing of the polyol and isocyanate components, and also to prevent mixing of water with the isocyanate in self-expanding embodiments, until it is desired to initiate curing. For convenience, the polyol and isocyanate components are referred to herein as the first precursor component and second precursor component, respectively. When water is present, it is included with the polyol in the first precursor component so that the water and the polyol can be mixed with the isocyanate at the same time to initiate both reactions simultaneously. Additional ingredients (i.e., ingredients other than the polyol and isocyanate components), if present, can be mixed with either the first precursor component or the second precursor component prior to initiating cure. In one embodiment, the additional components, if present, are mixed with the first precursor component (i.e., the polyol component). In one embodiment, the polyol component comprises from about 50 to about 96 parts polyether polyol, from about 0.2 to about 6 parts surfactant, from about 0.05 to about 4 parts amine catalyst, from about 0.1 to about 20 parts water, and optionally also includes up to 96 parts polyester polyol, up to 2 parts metal based catalyst, up to 15 parts HFC blowing agent and/or up to 12 parts pentane blowing agent. At the time when it is desired to initiate curing, the first precursor component is mixed with the second precursor component (i.e., the isocyanate component), and the mixture is then placed in the void space for curing, as described above.

The proportion of cellulosic food material pieces 2 to foam matrix 3 in bait material 1 can vary. In one embodiment, the bait material includes an average of from about 5 to about 200 parts foam matrix to 100 parts cellulosic food material pieces, by weight. In another embodiment, the bait material includes an average of from about 5 to about 150 parts foam matrix to 100 parts cellulosic food material pieces, by weight. In yet another embodiment, the bait material includes an average of from about 5 to about 100 parts foam matrix to 100 parts cellulosic food material pieces, by weight. In still another embodiment, the bait material includes an average of from about 5 to about 50 parts foam matrix to 100 parts cellulosic food material pieces, by weight. In another embodiment, the bait material includes an average of from about 10 to about 40 parts foam matrix to 100 parts cellulosic food material pieces, by weight In one representative example of a method for making a composite bait material, the material is made by providing a first precursor component that includes a polyol (or optionally a mixture of multiple polyols), a catalyst, a surfactant and water; providing a second precursor component including an isocyanate; and providing a plurality of bait material pieces in a bait enclosure. The first and second components are then mixed, which initiates the curing process, and the mixture is poured into the bait enclosure, thereby entering the void space between the bait material pieces and the bait enclosure. As the mixture cures, it expands to fill additional portions of the void space. It is within the purview of a person of ordinary skill in the art to provide a sufficient quantity of ingredients such that, as the mixture cures, it fills substantially all of the void space in the bait enclosure, if desired. In some cases, it may be desirable to include a slight excess of the mixture to ensure that substantially the entire void space is filled with polyurethane foam at the completion of the curing reaction. In an embodiment that utilizes a mold as the bait enclosure, at the completion of the curing reaction, the composite bait material can be removed from the mold for subsequent use. In addition, a composite bait material removed from a mold can optionally be subjected to further processing prior to use, such as, for example, by roughening the surface of the composite bait material to improve termite penetration. If curing is accomplished in a bait container, the bait material within the bait container is ready for use as a termite control device upon completion of curing, optionally with surface roughening at exposed surfaces of the composite bait material.

In one embodiment, polyurethane foam matrix 3 of composite bait material 1 comprises a rigid, closed-cell polyurethane foam. In other alternative embodiments, polyurethane foam matrix 3 of composite bait material 1 is a flexible closed-cell polyurethane foam, a rigid open-cell polyurethane foam or a flexible open-cell polyurethane foam. The foam matrices having these different physical properties can be made by adjusting the ingredients included in the mixture of polyurethane foam precursors, and is within the purview of a person of ordinary skill in the art. It is understood that a wide variety of polyurethane foam precursors and also a wide variety of process parameters (such as temperature and pressure) can be used to provide composite bait materials having various physical characteristics. It is within the ability of a skilled artisan, armed with the description of the present application, to select, without undue experimentation, advantageous combinations of polyurethane foam precursors and parameters to provide articles having differing physical features, such as, for example, different densities and rigidities.

When a stand-alone bait material is made using a mold, food material pieces 2 can be held away from the walls of the mold cavity to ensure that a continuous polyurethane foam barrier is formed around food material pieces 2. This can be achieved, for example, by positioning one or more structures in the mold prior to introduction of food material pieces into the mold to hold the food material pieces away from the walls of the mold cavity, thereby providing a space between the food material and the walls of the mold cavity. With the food material spaced apart from the walls of the mold cavity in this way, expansion and curing of the polyurethane foam in the mold provides a substantially continuous layer of polyurethane foam that surrounds or substantially surrounds all of the food material in the mold. This can be achieved in a variety of ways within the purview of a person of ordinary skill in the art. As one example, a preformed hollow polyurethane tube having outer dimensions generally corresponding to the inner dimensions of the mold cavity can be placed in the mold before introducing the food material pieces into the mold, thereby spacing the food material pieces away from the walls of the mold cavity. In this approach, the preformed polyurethane tube will become integrated into the composite bait material and will become an integral part of matrix 3. In another embodiment, such hollow polyurethane tube can itself operate as a mold that becomes part of the composite bait material upon curing of the polyurethane foam precursors. As another example, the food material pieces can be placed in a separate container configured to be placed in the mold such that it is spaced apart from the walls of the mold cavity. The container can itself be composed of a cellulosic food material, or alternatively can be composed of a non-food material. If the container is composed of non-food material, it can have a screen-like, net-like or scaffold-like configuration, thereby providing openings suitable for passage of termites.

In another embodiment, composite bait material 1 includes a termite feeding enhancer (hereafter "enhancer") integrally entrained in the polyurethane foam. The enhancer comprises a material that is dispersible or soluble in the mixture of polyurethane foam precursors, and is thereby capable of becoming entrained in polyurethane foam matrix 3 as it cures to become an integral component of the polyurethane foam. In one embodiment, the enhancer comprises a dispersible or soluble food material (hereafter "food material enhancer"), such as, for example, a particulate cellulosic material or a sugar. In another embodiment, the enhancer comprises a non-food attractant, such as, for example, a natural or synthetic chemical or biochemical compound or mixture of compounds that is effective to enhance termite feeding or tunneling activity in a polyurethane foam comprising same (hereafter "chemical enhancer"). The term "sugar" is used herein to refer to a monosaccharide, disaccharide, polysaccharide or other carbohydrate substance that is an acceptable food for termites. The presence of a food material enhancer increases the palatability of the polyurethane foam to the termites, thereby increasing the attractiveness of the bait material to the termites.

To make a bait material including an enhancer, an enhancer is included in the uncured mixture of polyurethane foam precursors before the mixture is introduced into the void space in the bait enclosure and allowed to cure. For example, in one embodiment, alpha-cellulose powder is mixed into the polyol precursor component prior to mixing it with the isocyanate component to initiate the curing reaction. A bait material made in this manner includes the enhancer entrained in the polyurethane foam matrix, thereby enhancing the attractiveness and/or palatability of the polyurethane foam matrix. In one embodiment, a particulate cellulosic material is included in an amount that will produce a polyurethane foam having up to about 95 parts cellulose to 100 parts polyurethane, by weight. In another embodiment, a particulate cellulosic material is included in an amount that will produce a polyurethane foam having from about 1 to about 75 parts cellulose to 100 parts polyurethane, by weight. In another embodiment, a particulate cellulosic material is included in an amount that will produce a polyurethane foam having from about 1 to about 45 parts cellulose to 100 parts polyurethane, by weight. In yet another embodiment, a particulate cellulosic material is included in an amount that will produce a polyurethane foam having from about 5 to about 30 parts cellulose to 100 parts polyurethane, by weight. In still another embodiment, a particulate cellulosic material is included in an amount that will produce a polyurethane foam having from about 5 to about 25 parts cellulose to 100 parts polyurethane, by weight. In still yet another embodiment, a particulate cellulosic material is included in an amount that will produce a polyurethane foam having from about 5 to about 20 parts cellulose to 100 parts polyurethane, by weight. The above proportions are directed to the amount of particulate cellulose material entrained in the polyurethane foam, and do not include the amount of cellulose that may additionally be included in cellulosic food material pieces that may also be encapsulated by the foam. As will be appreciated by a person skilled in the art in view of the present disclosure, the present application encompasses embodiments in which the composite bait material includes polyurethane foam encapsulating cellulosic food material pieces and also includes an enhancer is entrained in the polyurethane foam, embodiments in which cellulosic food material pieces are absent and the composite bait material includes an enhancer is entrained in the polyurethane foam, and embodiments in which the composite bait material includes polyurethane foam encapsulating cellulosic food material pieces and the enhancer is absent from the polyurethane foam.

In yet another manner of making a composite bait material, a food material enhancer, such as, for example, a sugar or a particulate cellulosic material, or a chemical enhancer is mixed into an uncured mixture of polyurethane foam precursors, and the mixture is introduced into an empty container, such as, for example, an empty bait container or an empty mold, for curing. In this embodiment, the food material enhancer entrained in the polyurethane foam is utilized as a food source for the termites, and cellulosic food material pieces 2 of composite bait material 1 can be omitted. In this embodiment, additional enhancers can optionally be included in addition to the food material enhancer. In yet another embodiment, an enhancer can be applied to cellulosic food material pieces 2 prior to forming the foam matrix. For example, pieces 2 can be soaked in or coated with a chemical enhancer or a solution of food material enhancer, such as, for example, a sugar solution, prior to formation of matrix 3.

The present application is not intended to be limited to the manufacture of bait material products having a specific shape. Rather, a wide variety of shapes are envisioned. Articles made in accordance with the application can be formed into a wide variety of shapes and sizes by mold design, by post-curing processing or by a combination thereof. In one embodiment, the composite bait material is contained within a bait tube as described further hereinbelow.

Figure 2:
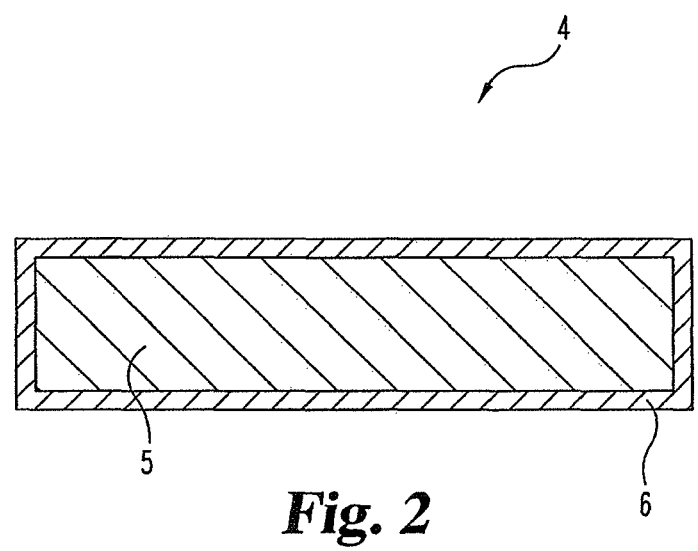
FIG. 2 is a cross sectional view of a composite bait material according to another embodiment of the present application.

Another aspect of the application is a moisture-resistant composite bait material that includes a cellulosic food material member that is palatable to termites, encapsulated within a termite-edible or termite-displaceable polyurethane foam coating. The foam coating provides a water resistant barrier between the cellulosic food material member and its environment. With reference to the embodiment depicted in FIG. 2, composite bait material 4 includes cellulosic food material member 5 and polyurethane foam coating 6. Cellulosic food material member 5 can be composed of, for example and without limitation, an extruded cellulosic food material, a piece of wood, a termite-edible or termite-displaceable material for an ESP monitor or a termite-edible or termite-displaceable material for a HALO™ monitoring device. For example, member 5 can comprise a material including a thermoplastic polymer, such as, for example, a material made as described in the commonly-owned U.S. Patent Application Publication No. 2008/0187565. For example, cellulosic food material member 5 can be made by molding, extruding or otherwise processing a mixture of a thermoplastic material and a pest food material, with or without a pesticide included therein. Polyurethane foam coating 6 can also include an enhancer entrained therein, as described above in connection with polyurethane matrix 3.

Coating 6 can be applied to member 5, for example, by providing a first precursor component that includes a polyol (or optionally a mixture of multiple polyols), a catalyst, and optionally additional ingredients, such as, for example, a surfactant and water; providing a second precursor component including an isocyanate; and providing a cellulosic food material member. The first and second components are then mixed, which initiates the curing process, and the mixture is coated on the food material member to cure thereon. As the mixture cures, it produces a polyurethane coating over the surface of the food material member. The mixture can be coated on food material members in a variety of ways that would occur to a person of ordinary skill in the art. For example, in one manner of coating food material member 5, member 5 is dipped in the mixture, and then, after, withdrawing member 5 from the mixture, the mixture remaining on the surface of member 5 is allowed to cure. If desired, this process can be repeated one or more times to apply polyurethane foam coating 6 to member 5 in layers until a desired thickness is achieved. In another manner of applying coating 6 to member 5, the member is placed into a mold or other container, such as, for example, a polyethylene pipe having internal dimensions corresponding to the desired final dimensions of the composite bait material, which are greater than the dimensions of the extruded food material member. With the food material member positioned such that it does not contact the walls of the cavity defined by the mold or other container, the mixture is poured into the container, thereby entering the void space between the food material member and the walls of the cavity. As the mixture cures, it produces a polyurethane coating over the surface of the food material member, the coating having external dimensions corresponding to the internal dimensions of the cavity.

As stated above, bait materials described herein can be made without pesticides, or can optionally include one or more pesticides. In the manufacture of composite bait materials that include pesticides, the pesticide can be entrained in the food material or in the uncured mixture of polyurethane foam precursors for subsequent incorporation into the polyurethane foam. The term "food material" is used herein collectively to refer to cellulosic food material pieces, a food material enhancer, such as, for example, particulate cellulosic or sugar material, or a cellulosic food material member, depending upon the particular configuration of the composite bait material. For example, in one manner of incorporating a pesticide into a bait material, a particulate cellulosic material, such as, for example, purified alpha cellulose, is first pre-loaded with a pesticide. In one manner of preloading, the pesticide is sprayed directly on cellulose particles. The pesticide-treated cellulose particles can be incorporated directly into a mixture of polyurethane foam precursors as a food enhancer, as described above. Then, upon curing of the mixture, the pesticide-loaded particles become entrained in a polyurethane foam matrix. Alternatively, the pesticide-treated cellulose particles can be mixed with other materials for extrusion to form an extruded, pesticide-containing food material member. As yet another alternative, pesticide-treated cellulose particles can be compacted and broken into prills, which include the cellulose food material and the pesticide therein, and which can be used as food material pieces. In another manner of pre-loading the food material with a pesticide, pre-formed prills of cellulose (which are available commercially, and can be obtained from International Fiber) are sprayed with the pesticide to provide a pesticide-loaded cellulose material. The cellulose/pesticide prills can then be placed into a bait enclosure as described above for subsequent introduction of a mixture of polyurethane foam material precursors. Pesticides can also be sprayed onto other types of cellulosic food materials, such as, for example, wood blocks, cardboard, sawdust and the like, which can then be included in an uncured mixture of polyurethane foam precursors (in the case of sawdust or other particulate material) or placed into a bait enclosure for subsequent introduction of a mixture of polyurethane foam material precursors.

A pesticide alternatively can be incorporated into a composite bait material by mixing the pesticide directly into the mixture of polyurethane foam precursors. Upon curing of the mixture, a polyurethane foam having the pesticide entrained therein is formed. As yet another example, which can be employed in the manufacture of a bait material having an open-cell configuration, the pesticide can be incorporated into the bait material after the polyurethane foam is cured by soaking the bait material in a pesticide-containing fluid. Upon soaking, the pesticide will enter the pores of the polyurethane foam matrix, thereby becoming entrained therein. Moreover, if the bait material is allowed to soak for a sufficient period of time, the pesticide can move through the network of passages formed in the open-cell foam and come into contact with the cellulosic food material entrained in the polyurethane foam matrix, and become entrained in the food material also.

The pesticide is one that is effective to kill pests that ingest or contact the pesticide. Some of the pesticides that can be employed in a composite material as disclosed herein include, but are not limited to the following:

1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha cypermethrin, alpha ecdysone, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate, barium hexafluorosilicate, barthrin, benclothiaz, bendiocarb, benfuracarb, benomyl, benoxafos, bensultap, benzoximate, benzyl benzoate, beta cyfluthrin, beta cypermethrin, bifenazate, bifenthrin, binapacryl, bioallethrin, bioethanomethrin, biopermethrin, bistrifluoron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfuram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma cyhalothrin, gamma HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, omethoate, oxamyl, oxydemeton methyl, oxydeprofos, oxydisulfoton, paradichlorobenzene, parathion, parathion methyl, penfluoron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfuram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vamidothion, vaniliprole, vaniliprole, XMC, xylylcarb, zeta cypermethrin and zolaprofos.

Additionally, any combination of the above pesticides can be used.

For more information consult "Compendium of Pesticide Common Names" located at http://www.alanwood.net/pesticides/index.html as of the filing date of this document. Also consult "The Pesticide Manual" 14th Edition, edited by C D S Tomlin, copyright 2006 by British Crop Production Council.

In one embodiment, the pesticide is one that has an immediate effect upon ingestion by or contact with a pest (referred to herein as an "immediate action" pesticide or a "fast acting" pesticide). For example, insecticides that have immediate killing action upon ingestion by termites include chlorpyrifos, spinosad, imidacloprid and fipronil, each of which is well known and available commercially. As used herein, the terms "immediate action" and "fast acting" are intended to mean that the pesticide typically operates to kill an individual pest before the pest returns to its colony. In another embodiment, the pesticide is one that exhibits a delayed effect upon ingestion by or contact with a pest (referred to herein as a "delayed action" pesticide). For example, insecticides that have delayed killing activity upon ingestion by or contact with termites include hexaflumuron and noviflumuron, each of which is well known and available commercially. As used herein, the term "delayed action" is intended to mean that the pesticide typically does not operate to kill an individual pest until after the pest has returned to its colony. In another embodiment, the pesticide is selected from the group consisting of lufenuron, diflubenzuron, flufenoxuron and hydramethylnon.

In addition to the polyurethane foam, the food material and optionally a pesticide, other ingredients can optionally be included in the composite bait material. For example, some ingredients can be included to increase the stability or shelf life of the pesticide included in the composite. Other ingredients can be selected to improve the compatability of the substances present in the bait material, or to provide an advantageous effect after the bait material is formed. Still other ingredients can be selected, for example, as attractants to enhance the attraction of pests to the baits or to stimulate feeding. The composite materials disclosed herein can also include or be used with herbicides and fungicides, both for reasons of economy and synergy. The composite bait materials disclosed herein can also include or be used with antimicrobials, bactericides, defoliants, safeners, synergists, algaecides, attractants, desiccants, pheromones, repellants, animal dips, avicides, disinfectants, semiochemicals, and molluscicides (these categories not necessarily mutually exclusive) for reasons of economy, and synergy.

A composite bait material as provided herein can be used as a stand-alone bait for attracting and terminating pests as a single-step pesticide delivery tool without the need for monitoring by pest control professionals to determine whether such pests are present in a given area. Alternatively, it can be used as a bait for a pest control device or system that employs monitoring steps for determining the presence or absence of wood destroying pests. For example, it can be used as a replacement monitor or a pesticide-delivery bait in an already existing termite bait station such as, for example, a SENTRICON TERMITE COLONY ELIMINATION SYSTEM® bait station. Whether the bait material is used as a stand-alone bait or as a replacement monitor or bait in an already existing termite bait station, the foam operates to provide a physical barrier between the cellulosic food material and its environment. In some embodiments that include open-cell polyurethane foam, the foam operates to hold moisture in contact with the bait material. In other embodiments, including those that include closed-cell polyurethane foam, and some open-cell embodiments, when the device is exposed to environmental moisture, the foam is operable to reduce or prevent exposure of the bait to the environmental moisture.

Thus, in another aspect, the present application provides a pest control device that includes a composite bait material including a cellulosic food material and a polyurethane foam. In one form, a moisture-resistant termite control device includes a bait container that defines one or more slots, holes and/or apertures for access by termites and that includes a chamber for containing the composite bait material. The bait container also includes an upper end portion defining an upper opening into the chamber, a closure to selectively access and close the upper opening, a side wall and a lower end portion defining a bottom terminus of the bait container. The container may be placed in the cavity of an in-ground housing previously installed in the ground or may be used without such a housing. In another embodiment, the device includes a container, such as, for example, a bait tube, that includes polyurethane foam but does not include a cellulosic food material. Alternatively or additionally, the container may include a sensor to detect pest presence. The sensor can be embedded in polyurethane foam without a cellulosic food material, or can be embedded in a composite bait material that includes a cellulosic food material and a polyurethane foam. The pest control system 20 of FIGS. 3-11 provides a further example of such an implementation.

Figure 3:
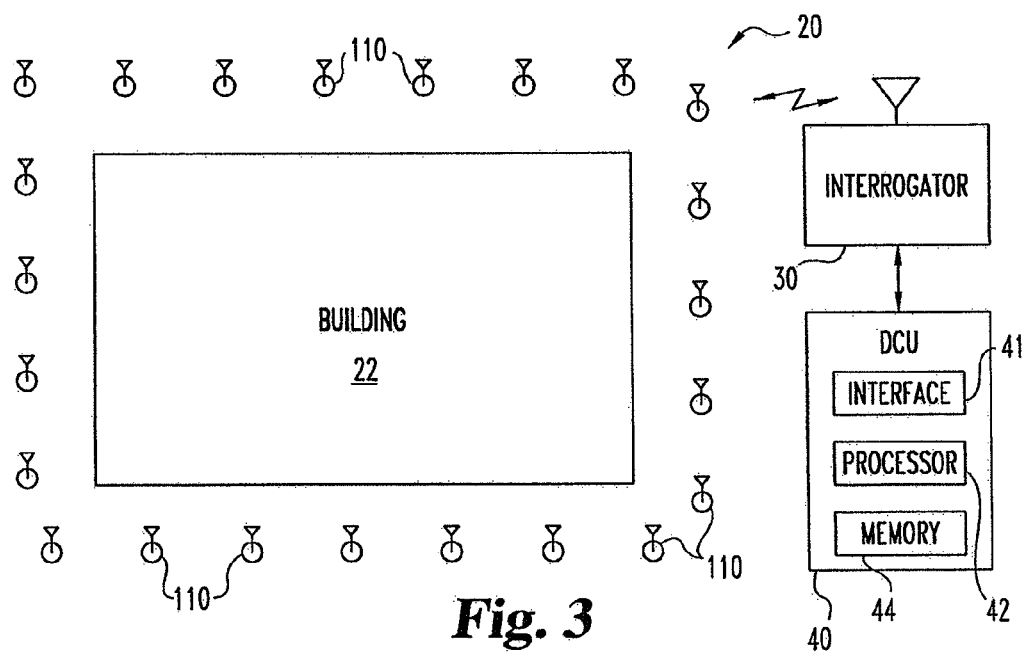
FIG. 3 is a diagrammatic view of a pest control system according to the present application that includes several pest control devices.

FIG. 3 illustrates pest control system 20. System 20 is arranged to protect building 22 from damage due to pests, such as subterranean termites. System 20 includes a number of pest control devices 110 positioned about building 22. In FIG. 3, only a few of devices 110 are specifically designated by reference numerals to preserve clarity. System 20 also includes a portable interrogator 30 to gather information about devices 110. Data gathered from devices 110 with interrogator 30 is collected in Data Collection Unit (DCU) 40 through communication interface 41. In other implementations, DCU 40 may not be present or only optionally utilized, instead using interrogator 30 as the terminal data gathering equipment.

Figure 4:
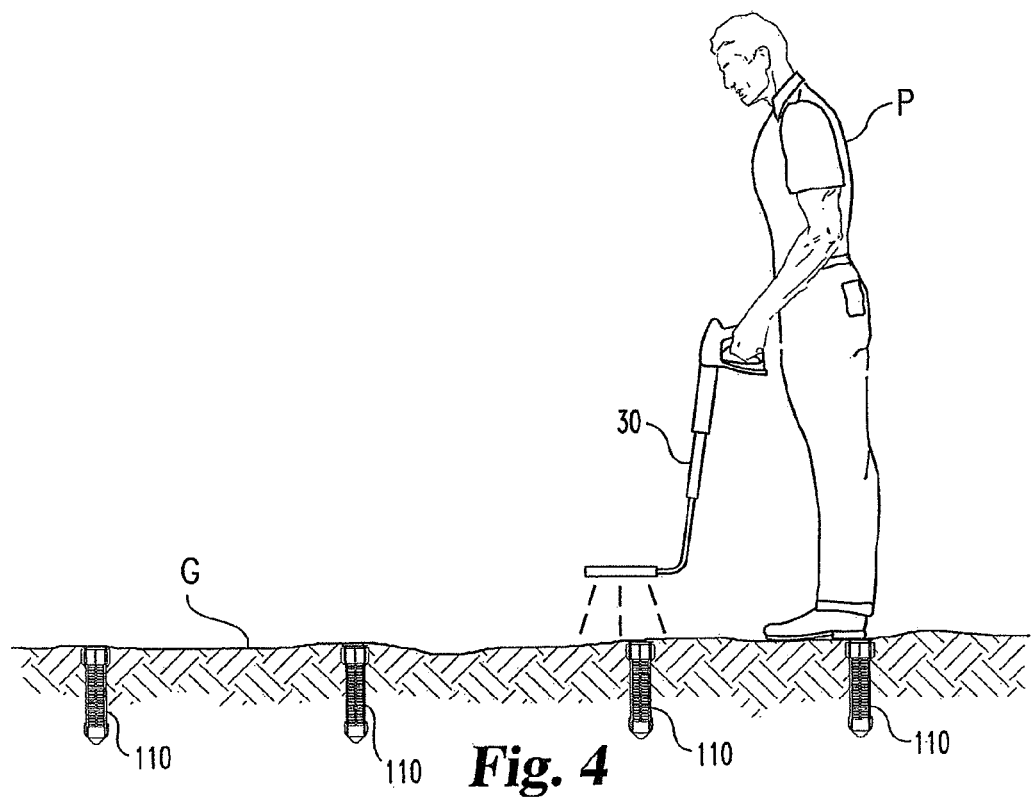
FIG. 4 is a further view of selected aspects of the system of FIG. 3 in operation.

Referring additionally to FIG. 4, certain aspects of the operation of system 20 are illustrated. In FIG. 4, a pest control service provider P is shown operating interrogator 30 to interrogate pest control devices 110 located at least partially below ground G using a wireless communication technique that does not require electrical contact between interrogator 30 and device 110 as further explained hereinafter. In this example, interrogator 30 is shown in a handheld form convenient for sweeping over ground G to establish wireless communication with installed devices 110. As an alternative or in addition to this contactless technique, interrogator 30 may make electrical and/or mechanical contact with each device 110 to gather data. In lieu of or along with interrogator 30, information about each pest control device 110 can be reported in a different manner, such as with a visual and/or aural indicator fixed to device 110 in still other embodiments.

Figure 5:
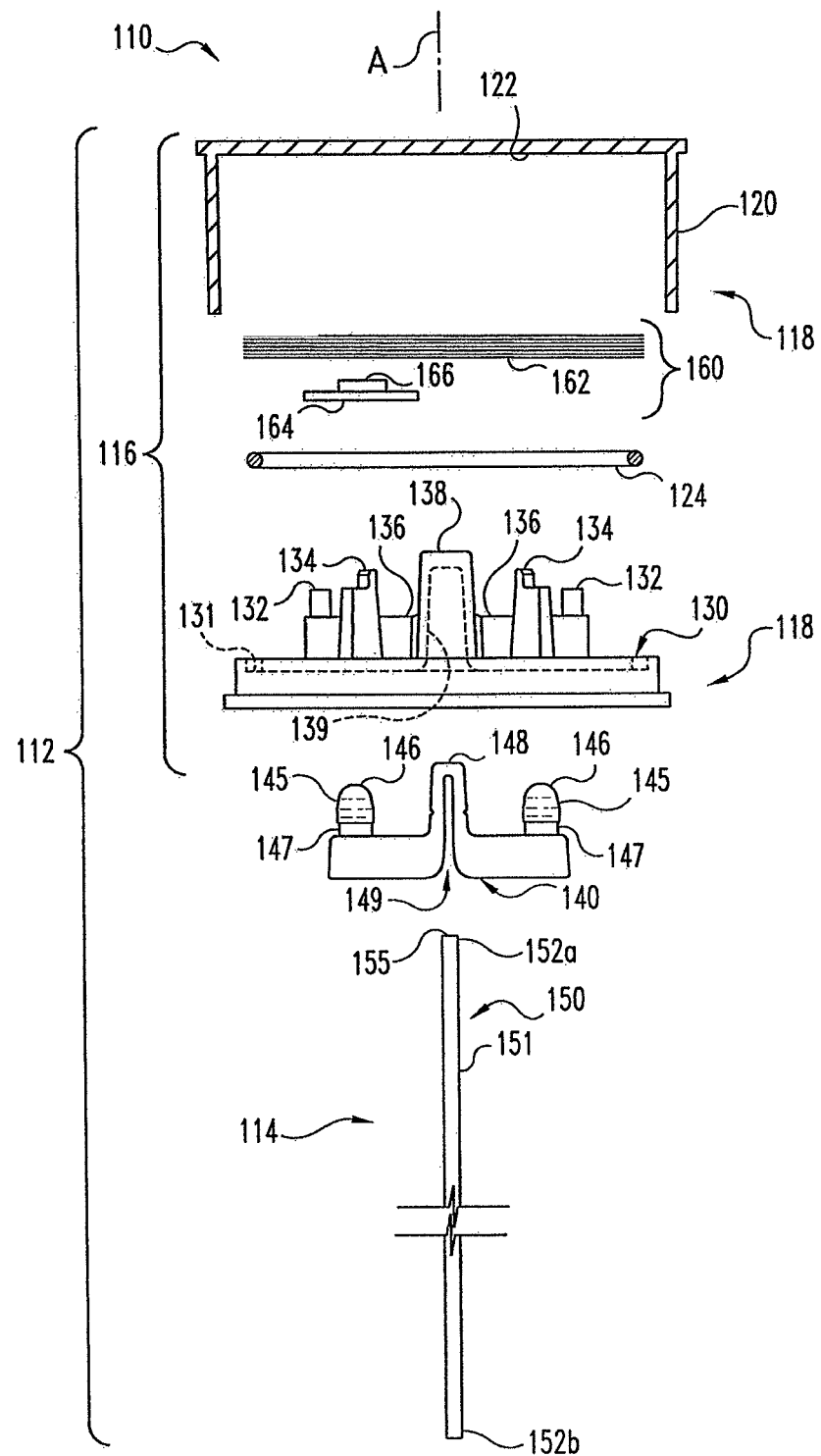
FIG. 5 is a partial, exploded sectional view of a pest monitoring assembly of one of the pest control devices.
Figure 6:
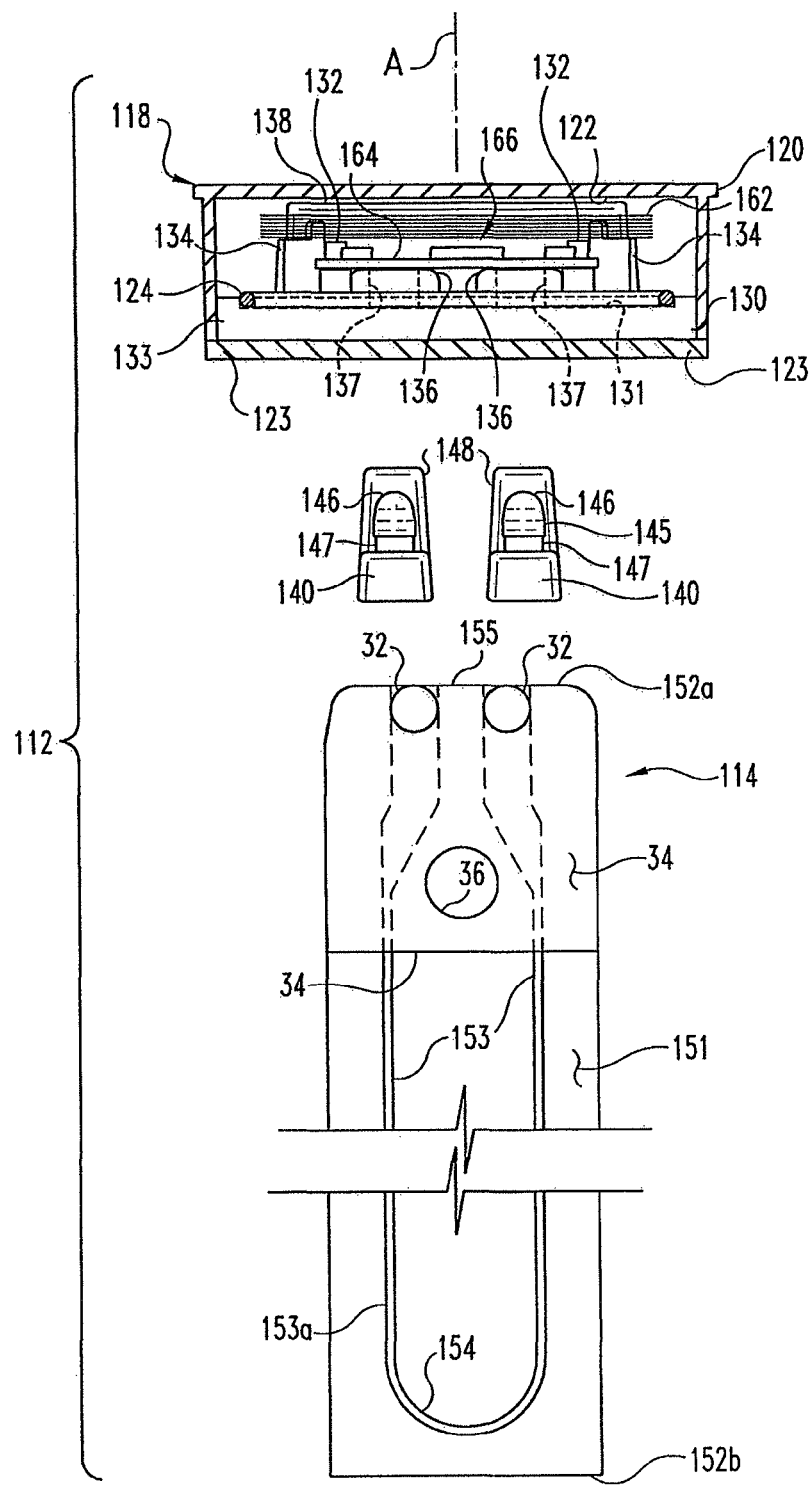
FIG. 6 is a partial, exploded sectional view of the pest monitoring assembly of FIG. 5 along a view plane perpendicular to the view plane of FIG. 5.

FIGS. 5-11 illustrate various features of pest control device 110. To detect pests, and optionally apply a pesticide, pest control device 110 is internally configured with pest monitoring assembly 112 structured for assembly in a bait container as further described in connection with FIGS. 8-11. Referring more specifically to FIGS. 5 and 6, pest monitoring assembly 112 is illustrated in part along centerline assembly axis A. Axis A coincides with the view planes of both FIGS. 5 and 6; where the view plane of FIG. 6 is perpendicular to the view plane of FIG. 5.

Pest monitoring assembly 112 includes sensor subassembly 114 below communication circuit subassembly 116 along axis A. Sensor subassembly 114 includes sensor 150. Sensor 150 is structured for contact with bait as more fully described hereinafter in connection with FIGS. 11 and 12; however, certain details of sensor 150 are described first as follows. Sensor 150 is generally elongated and has end portion 152a opposite end portion 152b as shown in FIGS. 5 and 6, for example. A middle portion of sensor 150 is represented by a pair of adjacent break lines separating portions 152a and 152b in FIGS. 5 and 6. Sensor 150 includes sensing substrate 151. Substrate 151 carries conductor 153 that is arranged to provide sensing element 153a in the form of an electrically conductive loop or pathway 154 shown in the broken view of FIG. 6. Along the middle sensor portion represented by the break lines of FIG. 6, the two segments of pathway 154 continue along a generally straight, parallel route (not shown), and correspondingly end at contact pads 32 at along an edge of end portion 152a. While one shape for pathway 154 is depicted in FIG. 6, the present application contemplates that alternative shapes can be utilized, it being understood that the ultimate goal is to increase the likelihood of detecting termites that are feeding in the area of element 153a. An electrically insulating film 34 covers a portion of each of the segments along end portion 152a. The film-covered segment portions are shown in phantom. Aperture 36 is formed through substrate 151 between the segments covered by film 34 that may be used for manufacturing and/or handling. At end portion 152b, the segments join each other to form pathway 154, completing the electrically conductive loop.

Substrate 151 and/or conductor 153 are/is comprised of one or more materials susceptible to consumption or displacement by the pests being monitored with pest monitoring assembly 112. These materials can be a food substance, a nonfood substance, or a combination of both for the one or more pest species of interest. Indeed, it has been found that materials composed of nonfood substances will be readily displaced during the consumption of adjacent edible materials by termites. As substrate 151 or conductor 153 are consumed or displaced, pathway 154 is eventually altered. This alteration can be utilized to indicate the presence of pests by monitoring one or more corresponding electrical properties of pathway 154 as will be more fully described hereinafter. Alternatively, substrate 151 and/or conductor 153 can be oriented with respect to bait members 132 so that a certain degree of consumption or displacement of bait members 132 exerts a mechanical force sufficient to alter the electrical conductivity of pathway 154 in a detectable manner. For this alternative, substrate 151 and/or conductor 153 need not be directly consumed or displaced by the pest of interest.

In one embodiment directed to subterranean termites, substrate 151 is formed from a cellulose material that is consumed, displaced, or otherwise removed by the termites. One specific example includes a paper coated with a polymeric material, such as polyethylene. In other embodiments, substrate 151 may be composed of different materials that target termites and/or other pests of interest.

In one form, conductor 153 is provided by a carbon-based conductive material, such as a carbon-containing ink compound. One source of such ink is the Acheson Colloids Company with a business address of 1600 Washington Ave., Port Huron, Mich. 48060. Carbon-containing conductive ink comprising conductor 153 can be deposited on substrate 151 using a silk screening, pad printing, or ink jet dispensing technique; or such other technique as would occur to those skilled in the art. Compared to commonly selected metallic conductors, a carbon-based conductor can have a higher electrical resistivity. Preferably, the volume resistivity of the carbon-containing ink compound is greater than or equal to about 0.001 ohm-cm (ohm-centimeter). In a more preferred embodiment, the volume resistivity of conductor 153 comprised of a carbon-containing material is greater than or equal to 0.1 ohm-cm. In a still more preferred embodiment, the volume resistivity of conductor 153 comprised of a carbon-containing material is greater than or equal to about 10 ohms-cm. In yet other embodiments, conductor 153 can have a different composition or volume resistivity as would occur to those skilled in the art. One example of an ink that is suitable for use as described above is Electrodag 423SS, which is commercially available from Acheson Colloids Company.

Pest monitoring assembly 112 further includes circuit subassembly 116 removably connectable to sensor subassembly 114. Circuit subassembly 116 is arranged to detect and communicate pest activity as indicated by a change in one or more electrical properties of pathway 154 of sensor subassembly 114. Circuit subassembly 116 includes circuit enclosure 118 for communication circuitry 160 and a pair of connection members 140 for detachably coupling communication circuitry 160 to sensor 150 of sensor subassembly 114. Enclosure 118 includes cover piece 120, o-ring 124, and base 130, that each have a generally circular outer perimeter about axis A. Enclosure 118 is shown more fully assembled in FIG. 6 than in FIG. 5. Cover piece 120 defines cavity 122. Base 130 defines channel 131 (shown in phantom) sized to receive o-ring 124 (see FIG. 6). As an alternative or addition to the O-ring 124, a heat seal may be used.

Figure 7:
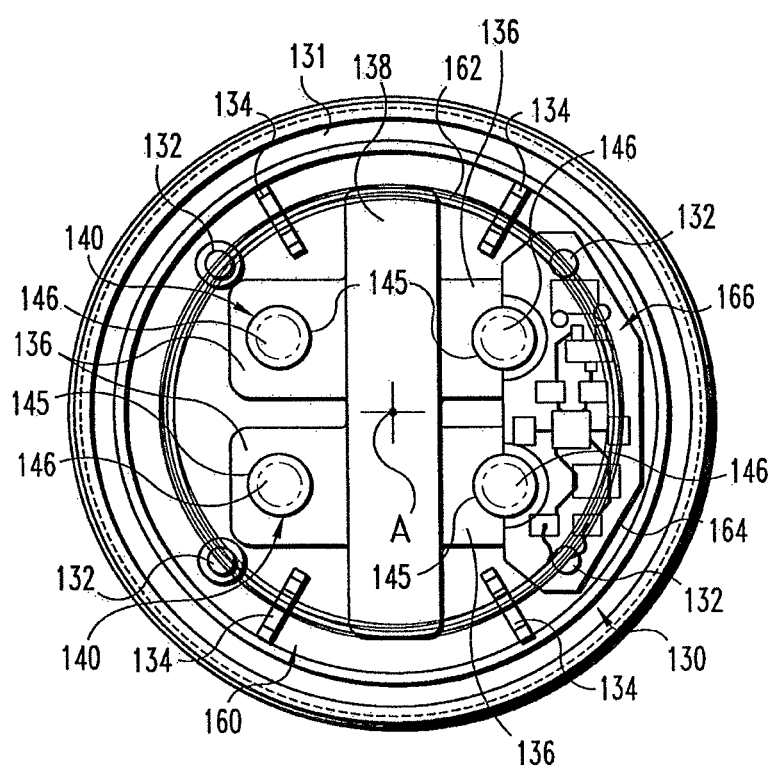
FIG. 7 is a partial, top view of a portion of a communication circuit subassembly of the pest monitoring assembly shown in FIGS. 5 and 6.

Communication circuitry 160 is positioned between cover piece 120 and base 130. Communication circuitry 160 includes coil antenna 162 and printed wiring board 164 carrying circuit components 166. Referring also to FIG. 7, a top view is shown of an assembly of base 130, connection members 140, and wireless communication circuitry 160. In FIG. 7, axis A is perpendicular to the view plane and is represented by like labeled cross-hairs. Base 130 includes posts 132 to engage mounting holes through printed wiring board 164. Base 130 also includes mounts 134 to engage coil antenna 162 and maintain it in fixed relation to base 130 and printed wiring board 164 when assembled together. Base 130 further includes four supports 136 each defining opening 137 therethrough as best illustrated in FIG. 6. Base 130 is shaped with a centrally located projection 138 between adjacent pairs of supports 136. Projection 138 defines recess 139 (shown in phantom in FIG. 5).

Referring generally to FIGS. 5-7, connection members 140 each include a pair of connection nubs 146. Each nub 146 has neck portion 147 and head portion 145 that extend from opposing end portions of the respective connection member 140. For each connection member 140, projection 148 is positioned between the corresponding pair of nubs 146. Projection 148 defines recess 149. Connection members 140 are formed from an electrically conductive, elastomeric material. In one embodiment, each connection member 140 is made from a carbon-containing silicone rubber, such as compound 862 available from TECKNIT USA, having a business address of 135 Bryant Street, Cranford, N.J. 07016. In other embodiments, a different composition can be used.

To assemble each connection member 140 to base 130, the corresponding pair of nubs 146 is inserted through a respective pair of openings 137 of supports 136, with projection 148 extending into recess 139. Head portion 145 of each of nubs 146 is sized to be slightly larger than the respective opening 137 through which it is to pass. As a result, during insertion, head portions 145 are elastically deformed until fully passing through the respective opening 137. Once head portion 145 extends through opening 137, it returns to its original shape with neck 147 securely engaging the opening margin. As shown in FIG. 7, printed wiring board 164 contacts one nub 146 of each connection member 140 after assembly.

Once connection members 140 are assembled with base 130, enclosure 118 is assembled by connecting base 130 to cover piece 120 with o-ring 124 carried in channel 131. A potting compound may be used inside the resulting structure to reduce moisture intrusion and/or other foreign agents. Further, as previously noted, a heat sealing technique can be used in addition to or in lieu of the o-ring 124/channel 131 structure. After communication circuit subassembly 116 is assembled, sensor 150 is assembled to subassembly 116 by asserting end portion 152a into recess 149 of each connection member 140 carried by base 130. Connection members 140 are sized to be slightly elastically deformed by the insertion of end portion 152a into recess 149, such that a biasing force is applied by connection members 140 to end portion 152a to securely hold sensor 150 in contact therewith. Once end portion 152a is inserted into connection members 140, each pad 32 is electrically contacted by a different one of connection members 140. In turn, each nub 146 that contacts printed wiring board 164 electrically couples pathway 154 to printed wiring board 164.

Figure 8:
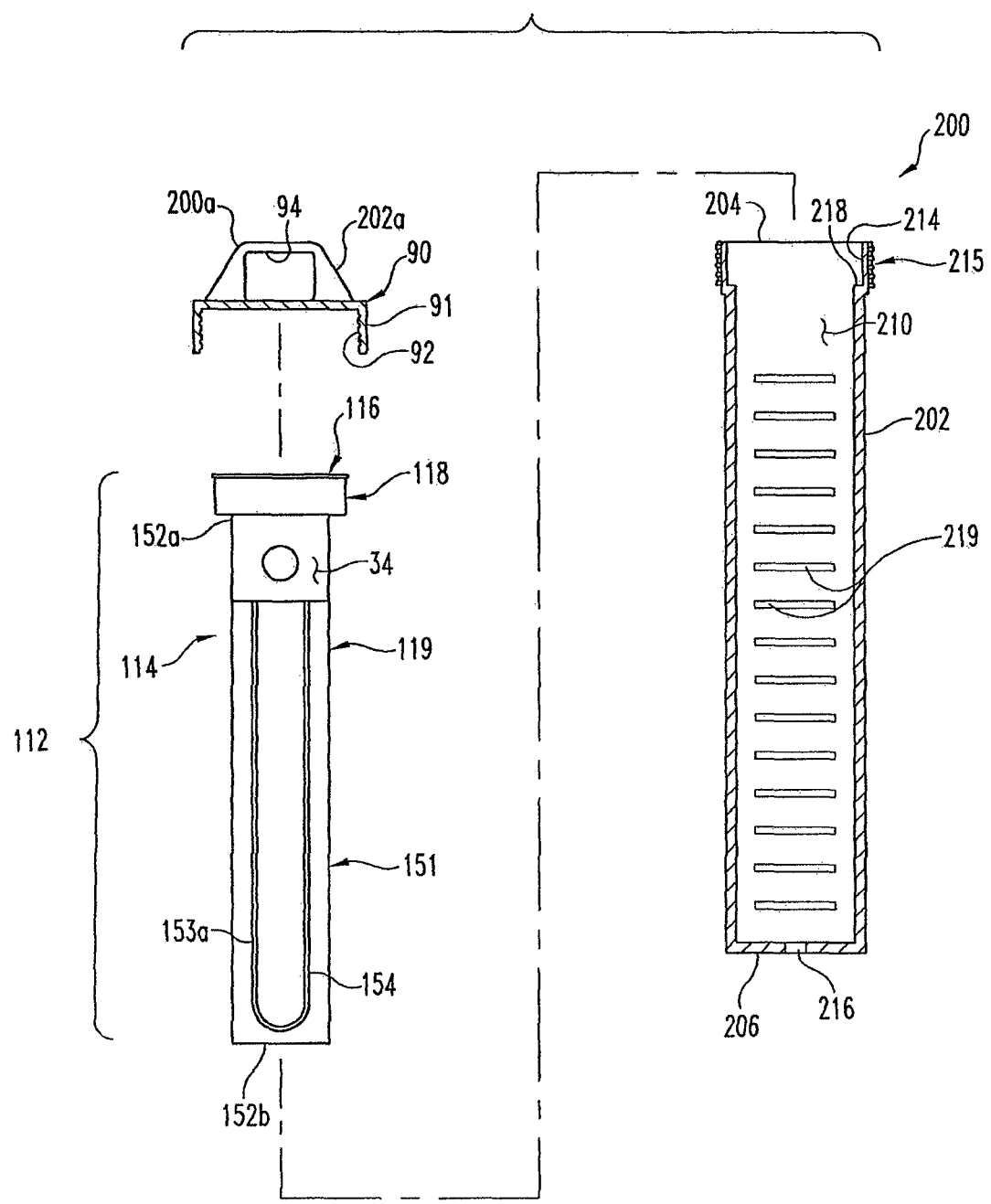
FIG. 8 is an exploded view of a bait container of one of the pest control devices of the pest control system depicted in FIG. 3, including the pest monitoring assembly of FIG. 5.

FIG. 8 illustrates the resulting assembly of subassembly 114 and 116 as part of an exploded view of a higher assembly stage of pest control device 110. In FIG. 8, pest monitoring assembly 112 is alternatively designated sensing assembly 119, and collectively represents the assembled form of subassemblies 114 and 116. Once assembled, sensing assembly 119 is structured to facilitate installation and other handling as a unit. FIG. 8 also depicts bait container 200 in exploded form, which includes sensing assembly 119 when fully assembled. Bait container 200 also includes a tubular body 202 with an upper end portion 204 opposite a lower end portion 206. Body 202 is hollow to define interior space 210 to receive bait as more fully described hereinafter. Upper end portion 204 defines upper opening 214 that intersects interior space 210, lower end portion 206 defines lower opening 216 that also intersects interior space 210, and body 202 also defines side slots 219 between upper end portion 204 and lower end portion 206 that also intersect interior space 210. Accordingly, openings 214 and 216 and side slots 219 are in fluid communication with each other. Upper end portion 204 defines exterior helical threading 215 about opening 214.

Figure 9:
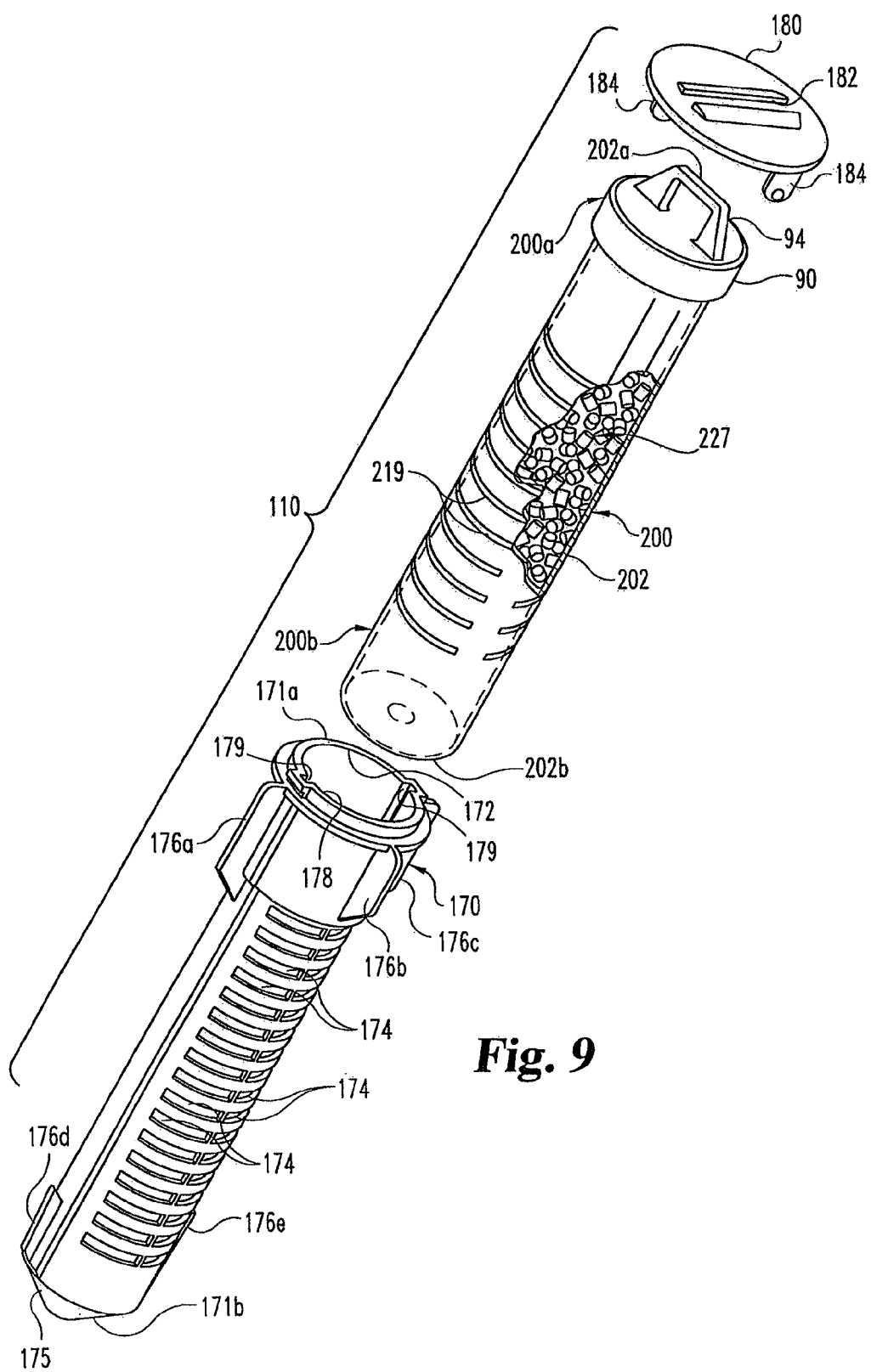
FIG. 9 is a perspective exploded view of the pest control device assembly of FIG. 8 with a diagrammatic cut away of the bait container and a diagrammatic cut away of the composite bait material, and further showing a ground installable housing of one of the pest control devices.
Figure 10:
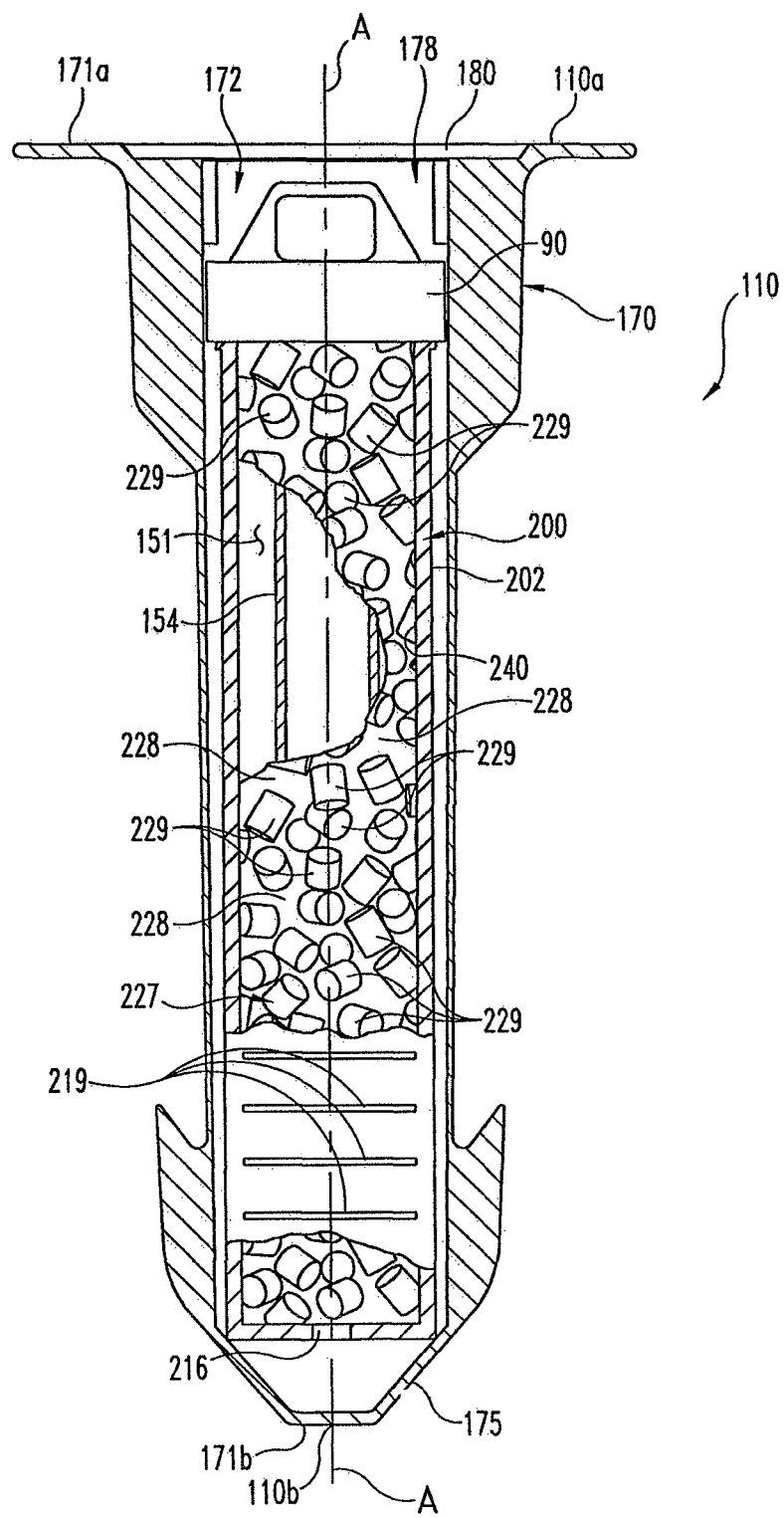
FIG. 10 is a side, diagrammatic partial sectional, partial cutaway view of the assembly of FIG. 9.

Sensing assembly 119 is sized and shaped to be received in interior space 210 of container 200 through upper opening 214. Upper end portion defines a ledge to provide seat 218 upon which enclosure 118 of assembly 119 is structured to rest, suspending substrate 151 below in interior space 210 (See also the views of FIG. 9 and FIG. 10) when assembly 119 is placed therein. Bait container 200 (and correspondingly pest control device 110) further includes closure 90 in the form of a cap 91. Closure 90 includes interior threading 92 structured to engage exterior threading 215 of upper end portion 204 of body 202. Cap 91 includes handle 94 structured for grasping by hand or some type of an extraction tool to carry and otherwise manipulate bait container 200 when closure 90 is threadingly attached to container 200 as further described hereinafter. Closure 90 can be selectively rotated relative to upper end portion 204 to be threaded thereto and provide a seal. This state is illustrated in FIGS. 9 and 10. Accordingly, after insertion of assembly 119 in interior space 210, closure 90 can be engaged to upper end portion 204, and likewise can be removed to access assembly 119 as desired.

In addition to containing assembly 119, interior space 210 also contains composite bait material 227 (shown in FIGS. 9 and 10). Bait material 227 is comprised of a multiple cellulosic food material pieces 229 embedded in polyurethane foam matrix 228. Composite bait material 227 conforms to the shape of interior space 210 occupying a geometric center thereof and spanning across its longitudinal centerline A. Nonetheless, in other embodiments, bait material 227 may be differently composed to target to a different pest type, may include more or fewer cellulosic food material pieces, may include a single food material piece such as a wood or synthetically formed cellulose block, may include an attractant with or without pesticide, and/or may be otherwise differently constituted.

To assemble bait container 200, sensing assembly 119 is placed in interior space 210 of body 202 through proximal end portion 204 to engage upper seat 218. After placement of sensing assembly 119 in body 202, closure 90 is threaded on proximal end portion 204 to close opening 214. Container 200 is inverted to load cellulosic food material pieces 229 through opening 216 to at least partially fill interior space 210. In one form, cellulosic food material pieces 229 are distributed along opposite sides of substrate 151. The body 202 may include one or more interior slots and/or guide flanges (not shown) to assist with maintaining substrate 151 in a desired position as food material pieces 229 are distributed thereabout. After loading cellulosic food material pieces 229, a mixture of uncured polyurethane foam precursors is then introduced into interior space 210 and allowed to flow into the void space in interior space 210 created by food material pieces 229 and body 202. The uncured polyurethane precursors can be introduced into interior space 210 by pouring through opening 216 in bait container body 202, as described above in connection with the manufacture of composite bait material 1. Alternative, a mixture of polyurethane foam precursors can be provided in a delivery system that includes a blowing agent, such as for example, the GREAT STUFF™ polyurethane foam system that is commercially available from The Dow Chemical Company. As the mixture of precursors cures to form polyurethane foam matrix 228, it expands to fill additional portions of the void space in interior space 210, and thereby substantially fill the void space.

A skilled artisan will appreciate that, when the mixture of polyurethane foam precursors is poured, blown or otherwise introduced into interior space 210, some or all of the mixture may escape interior space 210 through slots 219 unless slots 219 are covered during the time period between the time when the mixture of polyurethane foam precursors is introduced into space 210 and the time when curing of the polyurethane foam is complete. Thus, in one manner of making bait container 200, slots 219 are covered before the polyurethane foam precursors are introduced into interior space 210. Slots 219 can be covered, for example, by applying a plastic film, such as, for example, shrink wrap, over the sides of body 202 before introducing the precursors into interior space 210. In one embodiment, the plastic film is a tape having an adhesive on one side to temporarily attach the tape to container body 202. After the polyurethane foam has cured, and before bait container 200 is put to use, the plastic film is removed to expose the slots and the polyurethane foam through slots 219. When an adhesive tape is used to cover slots 219, removal of the tape can operate to roughen the exposed surface of polyurethane foam 228, which can increase the acceptance of composite bait material 228 to termites in the field. In one embodiment, body 202 also defines a small vent hole (not shown) to allow air to escape interior space 210 as the polyurethane foam cures, thereby equilibrating pressure in interior space 210 as the polyurethane foam cures. Alternatively, opening 216 can operate as a vent.

So assembled, bait container 200 includes body 202, sensing assembly 119, closure 90, and composite bait material 227; and collectively has upper end portion 200a opposite lower end portion 200b. Upper end portion 200a defines top terminus 202a of container 200 and lower end portion 200b defines bottom terminus 202b of container 200. Body 202 is generally annular/cylindrical; however, in other embodiments the shape of body 202 and one or more other components may vary with corresponding adjustments to accommodate assembly, coupling of components to one another, or the like as would occur to those skilled in the art. Body 202 and closure 90 are comprised of a material suitable for placement in the ground that resists removal/damage by pests that are expected to be present and degradation caused by the environment. In one nonlimiting form, the body 202 and closure 90 are made of an organic polymer compound.

FIGS. 9 and 10 illustrate housing 170 of pest control device 110. Housing 170 is arranged for installation in the ground G as shown, for example, in FIG. 4. Housing 170 defines a chamber or interior space 172 intersecting access opening 178. Bait container 200 is sized for insertion into interior space 172 through opening 178 without any portion of container 200 protruding above opening 178. Housing 170 has an access end portion 171a opposite a below-ground end portion 171b. End portion 171b includes tapered end 175 to assist with placement of pest control device 110 in the ground as illustrated in FIG. 4. End 175 terminates in an aperture (not shown). In communication with interior space 172 are preferably a number of passages 174 defined by housing 170. Passages 174 are particularly well-suited for the ingress and egress of termites from interior space 172. Housing 170 has a number of protruding flanges a few of which are designated by reference numerals 176a, 176b, 176c, 176d, and 176e in FIG. 9 to assist with positioning of pest control device 110 in the ground. Housing 170 includes removable cap 180 to cover opening 178. Cap 180 includes downward prongs 184 arranged to engage channels 179 of housing 170. After cap 180 is fully seated on housing 170, it can be rotated to engage prongs 184 in a latching position with a bayonet style connection that resists disassembly. Slot 182 can be used to engage cap 180 with a tool such as a top cap wrench, such as a flat-bladed screwdriver, to assist in rotating cap 180. Housing 170 and cap 180 can be made of a material resistant to deterioration by expected environmental exposure and resistant to alteration by the pests likely to be detected with pest control device 110. In one form, these components are made from a polymeric resin like polypropylene or CYCOLAC AR polymeric plastic material available from General Electric Plastics (One Plastics Avenue Pittsfield, Mass. 01201).

In a typical application directed to termite control, housing 170 is installed in ground with end portion 171b penetrating below ground level and end portion 171a being positioned approximately at ground level. With cap 180 removed, bait container 200 is inserted into space 172 of housing 170 through opening 178 to rest therein with lower end portion 200b entering first to be farther below ground level than upper end portion 200a. After placement of bait container 200 in housing 170 in-ground, cap 180 engages end portion 171a to cover opening 178. In relation to such operation and handling of housing 170 and container 200, portions 171a and 200a are also designated as proximal end portions, and portions 171b and 200b are also designated as distal end portions.

In one procedure implemented with system 20, a number of pest control devices 110 are installed in a spaced apart relationship relative to an area to be protected. By way of nonlimiting example, FIG. 3 provides a diagram of one possible distribution of a number of devices 110 arranged about building 22 to be protected. Typically each of devices 110 is at least partly below ground as illustrated in FIG. 4. It has been found that once a colony of termites establishes a pathway to a food source, they will tend to return to this food source. Consequently, devices 110 are placed in selected locations to establish such pathways with any termites that might be in the vicinity of the area or structures desired to be protected, such as building 22.

It has been found that baits installed in the ground are susceptible to various modes of degradation—many resulting from exposure to moisture. Typically, bait fouls or degrades/molds when it is saturated with water such as when the installed housing floods. Furthermore, when sensor 150 includes substrate 151 comprised of a moisture-alterable material, such as various types of paper or the like, it can be subject to water damage that results in a false indication of pest presence. By preventing food material pieces 229 and/or sensor 150 from being degraded in such a manner, the longevity and palatability of bait material 227 to targeted pests is enhanced and sensor 150 operation typically is more reliable. With reference to FIG. 10, inclusion of polyurethane foam matrix 228 reduces the chances of water reaching food material pieces 229 and sensor 150 by providing a barrier to moisture reaching food material pieces 229 and sensor 150. However, the composition of polyurethane foam matrix 228 facilitates removal by termites. Accordingly, as termites encounter housing 170, they pass through slots 219 and polyurethane foam matrix 228 to reach food material pieces 229. Because polyurethane foam matrix 228 is composed of a termite palatable or termite displaceable material, termites are likely to form passages therethrough to reach food material pieces 229. As a result, the moisture barrier presented by polyurethane foam seal 250 is breached as termites feed into composite bait material 227.

Figure 11:
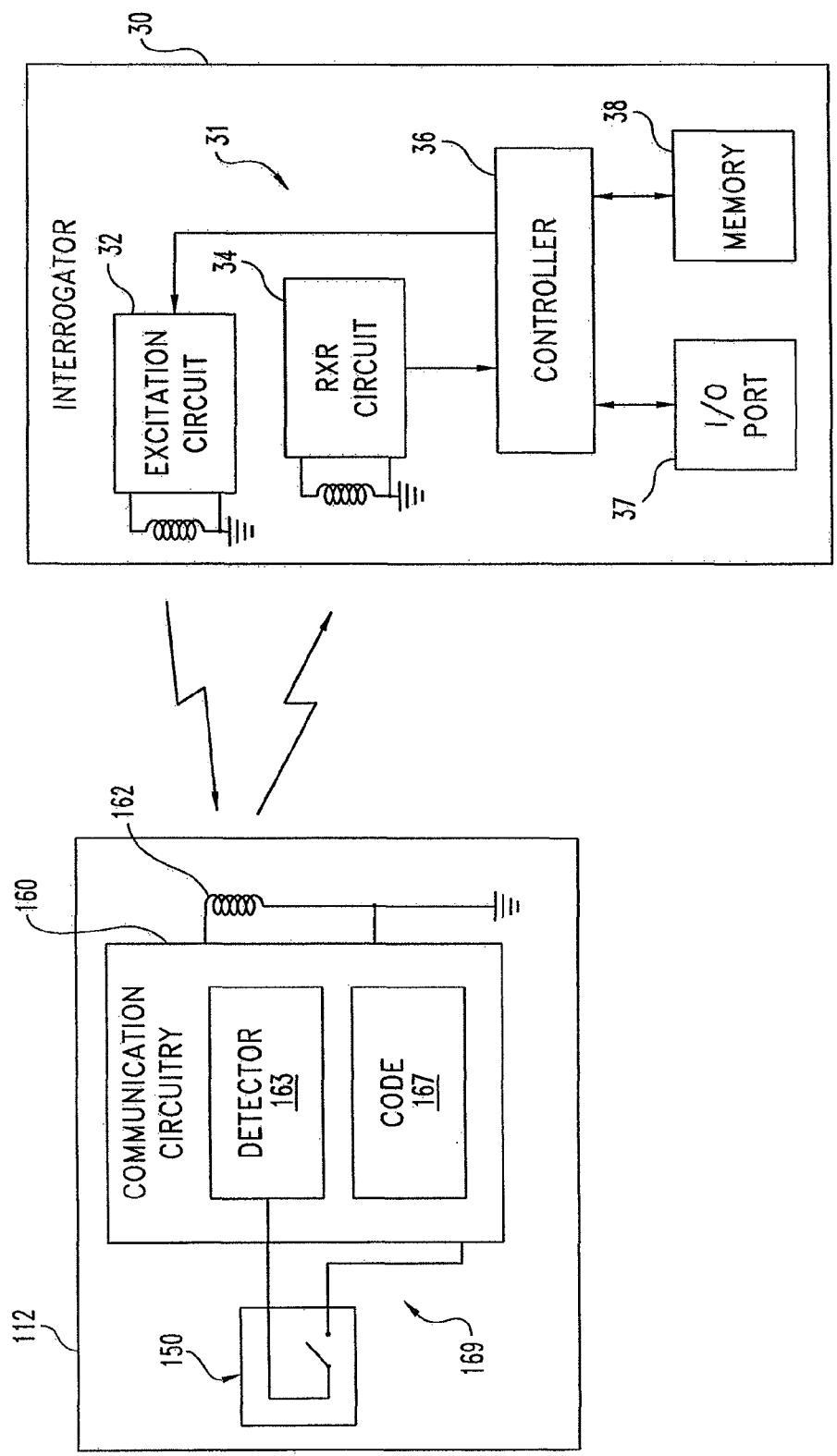
FIG. 11 is a schematic view of communication circuitry included in the pest control device of FIG. 8 and communication circuitry included the interrogator shown in FIGS. 3 and 4.

As termites reach bait 227 and invade chamber 240, alteration of substrate 151 is likely and eventually pathway 154 is broken, which can be used to signal the presence of termites with communication circuitry 160 of sensing assembly 119. In the depicted form, circuitry 160 is of a passive type that reports the status of pathway 154 in response to an external wireless signal from interrogator 30. FIG. 11 schematically depicts circuitry of interrogator 30 and pest monitoring assembly 112 for a representative pest control device 110. Monitoring circuitry 169 of FIG. 8 collectively represents communication circuitry 160 connected to conductor 153 of sensor 150 by connection members 140. In FIG. 11, pathway 154 of monitoring circuitry 169 is represented with a single-pole, single-throw switch corresponding to the capability of sensor 150 to provide a closed or open electrical pathway in accordance with pest activity. Further, communication circuitry 160 includes sensor state detector 163 to provide a two-state status signal when energized; where one state represents an open or high resistance pathway 154 and the other state represents an electrically closed or continuous pathway 154. Communication circuit 160 also includes identification code 167 to generate a corresponding identification signal for device 110. Identification code 167 may be in the form of a predetermined multibit binary code or such other form as would occur to those skilled in the art.

Communication circuitry 160 is configured as a passive RF transponder that is energized by an external stimulation or excitation signal from interrogator 30 received via coil antenna 162. Likewise, detector 163 and code 167 of circuitry 160 are powered by this stimulation signal. In response to being energized by a stimulation signal, communication circuitry 160 transmits information to interrogator 30 with coil antenna 162 in a modulated RF format. This wireless transmission corresponds to the termite presence determined with detector 163 and a unique device identifier provided by identification code 167. In alternate embodiments, power for signaling termite activity can be provided by one or more batteries.

FIG. 11 also illustrates communication circuitry 31 of interrogator 30. Interrogator 30 includes RF excitation circuit 32 to generate RF stimulation signals and RF receiver (RXR) circuit 34 to receive an RF input. Circuits 32 and 34 are each operatively coupled to controller 36. While interrogator 30 is shown with separate coils for circuits 32 and 34, the same coil may be used for both in other embodiments. Controller 36 is operatively coupled to Input/Output (I/O) port 37 and memory 38 of interrogator 30. Interrogator 30 has its own power source (not shown) to energize circuitry 31 that is typically in the form of an electrochemical cell, or battery of such cells (not shown). Controller 36 may be comprised of one or more components. In one example controller 36 is a programmable microprocessor-based type that executes instructions loaded in memory 38.

I/O port 37 is configured to send data from interrogator 30 to data collection unit 40 as shown in FIG. 3. Referring back to FIG. 3, further aspects of data collection unit 40 are described. Interface 41 of unit 40 is configured for communicating with interrogator 30 via I/O port 37. Unit 40 also includes processor 42 and memory 44 to store and process information obtained from interrogator 30 about devices 110. Processor 42 and memory 44 may be variously configured in an analogous manner to that described for controller 36 and memory 38, respectively. Further, interface 41, processor 42, and memory 44 may be integrally provided on the same integrated circuit chip.

Accordingly, for the depicted embodiment communication circuitry 160 transmits bait status and identifier information to interrogator 30 when interrogator 30 transmits a stimulation signal to device 110 within range. RF receiver circuit 34 of interrogator 30 receives the information from device 110 and provides appropriate signal conditioning and formatting for manipulation and storage in memory 38 by controller 36. Data received from device 110 may be transmitted to data collection unit 40 by operatively coupling I/O port 37 to interface 41.

After placement, installed devices 110 are periodically located and data is loaded from each device 110 by interrogation of the respective wireless communication circuit 160 with interrogator 30. This data corresponds to bait status and identification information. In this manner, pest activity in a given device 110 may readily be detected without the need to extract or open each device 110 for visual inspection. Further, such wireless communication techniques permit the establishment and building of an electronic database that may be downloaded into data collection device 40 for long term storage.

If status signal for a given device 110 indicates a broken pathway 154, the pest control service provider P can determine whether to visually inspect such device by removing cap 180 and closure 90, otherwise leaving pest control device in situ within the ground. Alternatively or additionally, the service provider could remove assembly 119 through the open proximal end portion 110a of device 110, provide an unaltered substrate 151 to continue monitoring termite activity, or replace container 200 completely. For example, container 200 can be replaced with a pesticide delivery device that includes a pesticide-containing bait, a variety of which are described herein. Such procedures can be repeated for any other devices 110 for which termite activity is detected. After termite activity is detected, periodic replenishment of bait may be performed with or without further monitoring with sensing assembly 119.

The present application also contemplates a wide variety of modifications to device 110 and, in particular, to container 200. For example, and without limitation, in another embodiment, food material pieces 229 can be omitted, and, in addition to containing sensing assembly 119, interior space 210 is filled with polyurethane foam, which can optionally include one or more enhancers entrained therein, as described above. A bait container of this embodiment can be assembled in the same manner as described above in connection with bait container 200, with the exception that no cellulosic food material pieces are loaded into interior space 210 before introducing the mixture of uncured polyurethane foam precursors. In yet another embodiment, sensing assembly 119 can be omitted, in which case interior space 210 is filled with composite bait material 227. This embodiment can be used, for example, as a monitoring device that can be checked by a service provider for termite activity by visual inspection. Alternatively, if a pesticide is included in composite bait material 227, this embodiment can be used as a pesticide delivery device. In yet another embodiment, sensing assembly 119 and food material pieces 229 can both be omitted, in which case interior space 210 is filled with polyurethane foam, which can optionally include one or more enhancers entrained therein, as described above. This embodiment can likewise be used, for example, as a monitoring device for visual inspection or as a pesticide delivery device.

Figure 12:
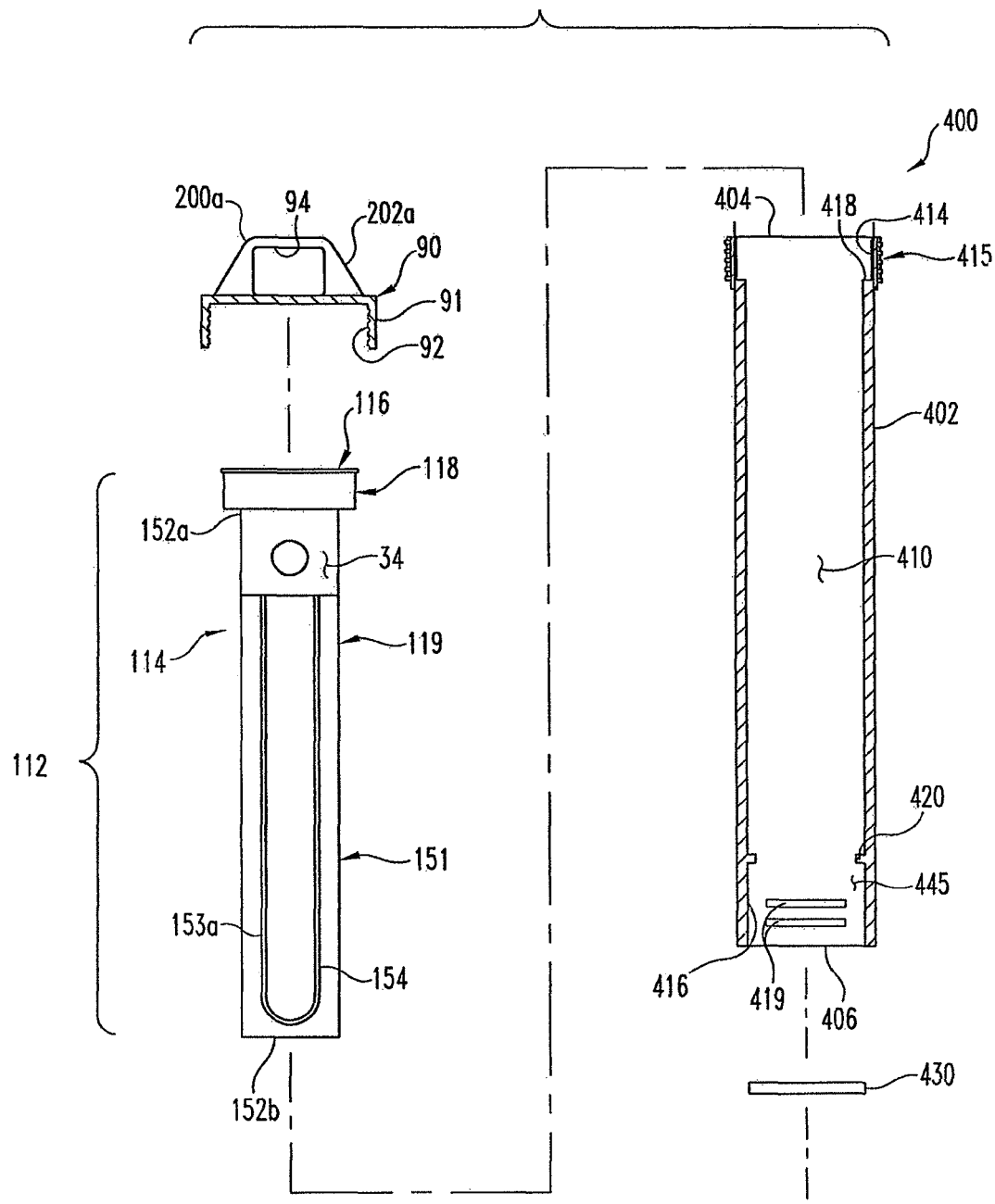
FIG. 12 is an exploded view of another embodiment bait container that can be used as a stand alone pest monitoring device or as one of the pest control devices of the pest control system depicted in FIG. 3, including the pest monitoring assembly of FIG. 5.
Figure 13:
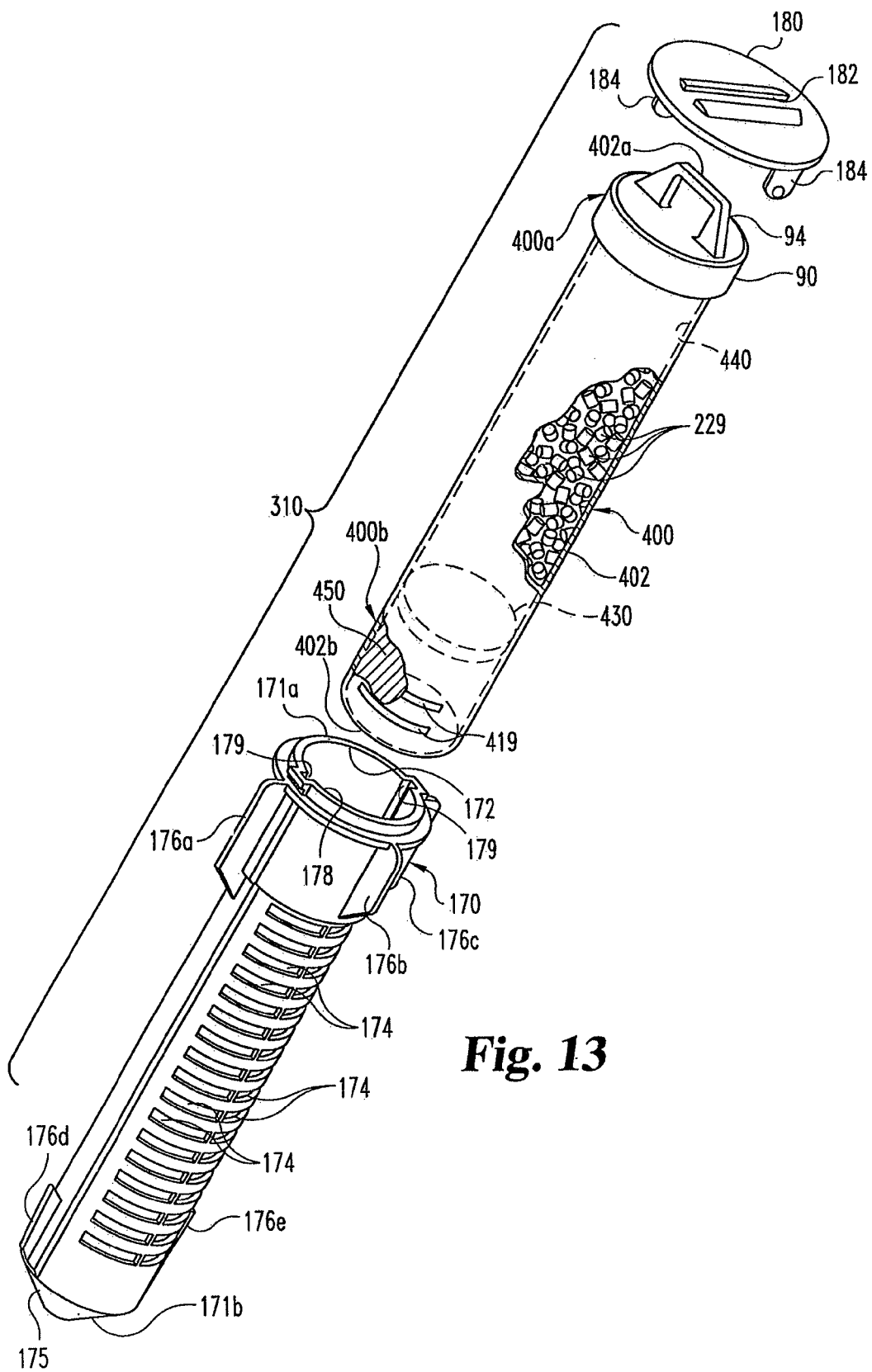
FIG. 13 is a perspective exploded view of the pest control device assembly of FIG. 12 with a diagrammatic cut away of the bait container and further showing a ground installable housing of one of the pest control devices.
Figure 14:
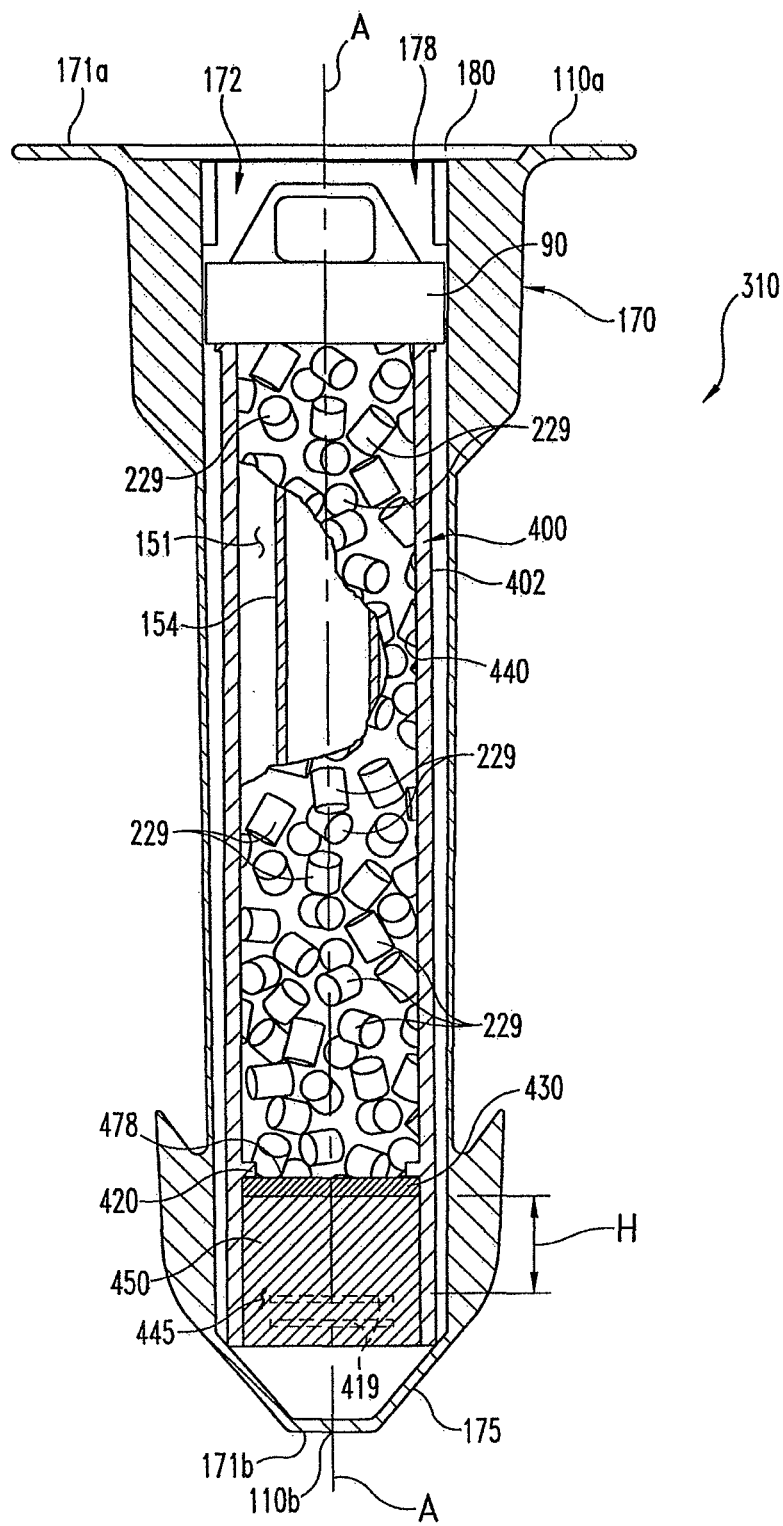
FIG. 14 is a side, diagrammatic partial sectional, partial cutaway view of the assembly of FIG. 13.

With reference now to FIGS. 12-14, the present application also provides a pest control device that includes a polyurethane foam component positioned at a location separate from cellulosic food material to provide a barrier between the food material and the environment of the device. The polyurethane foam component operates to seal a termite access opening in the device to provide a moisture barrier, thereby reducing bait damage cause by unwanted water intrusion into the device, for example, when the device is installed in the ground. In one embodiment, depicted in FIGS. 12-14, pest control device 310 is similar to pest control device 110 in certain respects, and can be substituted for device 110 in system 20 described above, but device 310 includes bait container 400 in place of bait container 200. FIG. 12, in a manner similar to FIG. 8, illustrates the resulting assembly of subassembly 114 and 116 as part of an exploded view of a higher assembly stage of pest control device 310. In FIG. 12, like FIG. 8, pest monitoring assembly 112 is alternatively designated sensing assembly 119, and collectively represents the assembled form of subassemblies 114 and 116. FIG. 12 also depicts bait container 400 in exploded form, which includes sensing assembly 119 when fully assembled. Bait container 400 also includes a tubular body 402 with an upper end portion 404 opposite a lower end portion 406. Body 402 is hollow to define interior space 410 to receive bait as more fully described hereinafter. Upper end portion 404 defines upper opening 414 that intersects interior space 410 and lower end portion 406 defines lower opening 416 and optional side openings 419 that also intersect interior space 410. Accordingly, openings 414, 416 and 419 are in fluid communication with each other prior to full assembly of bait container 400. Upper end portion 404 defines exterior helical threading 415 about opening 414 to receive and engage threading 92 on closure 90.

Sensing assembly 119 is sized and shaped to be received in interior space 410 of container 400 through upper opening 414. Upper end portion 404 defines a ledge to provide seat 418 upon which enclosure 118 of assembly 119 is structured to rest, suspending substrate 151 below in interior space 410 (See also the views of FIG. 13 and FIG. 14) when assembly 119 is placed therein. As described hereinabove, closure 90 includes interior threading 92 structured to engage exterior threading 415 of upper end portion 404 of body 402. Cap 91 includes handle 94 structured for grasping by hand or some type of an extraction tool to carry and otherwise manipulate bait container 400 as further described hereinafter. Closure 90 can be selectively rotated relative to upper end portion 404 to be threaded thereto and provide a water tight seal. This state is illustrated in FIGS. 13 and 14. Accordingly, after insertion of assembly 119 in interior space 410, closure 90 can be engaged to upper end portion 404, and likewise can be removed to access assembly 119 as desired.

Lower end portion 406 defines a ledge to provide seat 420 against which barrier 430 is structured to rest, held in place by polyurethane foam seal 450 that resides in chamber 445 after full assembly of bait container 400 (See also the views of FIG. 13 and FIG. 14). Barrier member 430 is shaped and sized to fit in interior space 410 through lower opening 416 to engage lower seat 420. In one form, barrier 430 is a disk comprised of a material that is consumable or displaceable by termites, such as, for example and without limitation, a sheet of cork, paper or wood. Barrier 430 divides interior space 410 of body 402 to define a lower boundary 478 of a bait containing chamber 440 in body 402, and separating bait containing chamber 440 from chamber 445 that is configured to contain a polyurethane foam seal. Body 400 also defines optional side slots 419 between lower boundary 478 of bait chamber 440 and bottom terminus 402a of bait container 400.

In one form targeted to termites, the bait contained in chamber 440 is comprised of multiple pellets 229 that each include a cellulosic food material attractive to termites and optionally also a pesticide. For this form, pellets 229 conform to the shape of chamber 410, occupying a geometric center thereof and spanning across its longitudinal centerline A. Nonetheless, in other embodiments, the bait may be differently composed to target to a different pest type, may include more or fewer pieces, may be a single piece such as a wood or synthetically formed cellulose block, may include an attractant with or without pesticide, and/or may be otherwise differently constituted.

To assemble bait container 400, sensing assembly 119 is placed in interior space 410 of body 402 through proximal end portion 404 to engage upper seat 418. After placement of sensing assembly 119 in body 402, closure 90 is threaded on proximal end portion 404 to close opening 414 with a water tight seal. Container 400 is inverted to load pellets 229 through opening 416 to at least partially fill the portion of interior space 410 that may reach up to lower seat 420. In one form, pellets 229 are distributed along opposite sides of substrate 151. Body 402 can optionally include one or more interior slots and/or guide flanges to assist with maintaining substrate 151 in a desired position as pellets 229 are distributed thereabout. Alternatively, sensing assembly 119 can be omitted. After loading pellets, barrier 430 is placed through opening 416 to engage lower seat 420. With barrier 430 positioned against lower seat 420, a mixture of uncured polyurethane precursors is then introduced into pocket 445 and allowed to cure to form water resistant polyurethane foam seal 450. The mixture of uncured polyurethane precursors can be made as described above, and can optionally include an enhancer entrained therein to increase its attractability to termites, if desired. So assembled, bait container 400 includes body 402, sensing assembly 119, closure 90, bait 227, barrier 430 and polyurethane foam seal 450; and collectively has upper end portion 400a opposite lower end portion 400b. Upper end portion 404 defines top terminus 402a of container 400 and lower end portion 406 defines bottom terminus 402b of container 400. In addition, if necessary or desired, after the polyurethane foam is cured, it can be trimmed at bottom terminus 402b of bait container 400 to a desired shape and/or size. In addition, lower surface of the polyurethane foam optionally can be roughened or otherwise treated to improve attractiveness of the surface to termites. Body 402, closure 90 and polyurethane foam seal 450 are generally annular/cylindrical; however, in other embodiments shape of one or more of these components may vary with corresponding adjustments to accommodate assembly, coupling of components to one another, or the like as would occur to those skilled in the art. Body 402 and closure 90 are comprised of a material suitable for placement in the ground that resists removal/damage by pests that are expected to be present and degradation caused by the environment. In one nonlimiting form, the body 402 and closure 90 components are made of an organic polymer compound. In an alternate embodiment, barrier 430 may be absent. In this embodiment, pellets 229 contact polyurethane foam seal 450 directly and are held in bait chamber 440 by polyurethane foam seal 450.

Referring to FIG. 14, container 400 is structured to reduce the chances of water reaching pellets 229. As initially installed, barrier 430 and polyurethane foam seal 450 each provide a barrier to moisture reaching lowermost boundary 478 of bait 229. Accordingly, when closure 90 is engaged to body 402 of container to form a seal therewith, this collective structure of container 400 provides a water-resistant boundary that surrounds bait chamber 440. However, the composition of barrier 430 and polyurethane foam seal 450 facilitates removal by termites. Accordingly, as termites enter housing 170 through openings 174, they encounter body 402 of bait container 400. When the termites encounter side openings 419 or lower opening 416 of bait container 400, they are able to tunnel through polyurethane foam seal 450 and barrier 430 to reach bait chamber 440. Because polyurethane foam seal 450 is composed of a termite palatable or termite displaceable material, termites are likely to form passages therethrough to reach barrier 430. Termites then form passages through barrier 430 to reach bait 227 in bait chamber 440. As a result of termites tunneling through polyurethane foam seal 450, the moisture barrier provided by polyurethane foam seal 450 is breached; however, by providing an airtight seal between closure 90 and body 402, the configuration depicted in FIGS. 12-14 also operates to provide moisture resistance even after polyurethane foam seal 450 is breached by tunneling termites. Specifically, because the only entry points for termites into bait chamber 440 are below the bait chamber 440, air that is trapped in interior space 410 of bait container 400 prevents water from entering bait chamber 440 under flooding conditions, even after termites have tunneled through polyurethane foam seal 450 and barrier 430. For example, if water level in the ground extends higher than the highest external entry point of termites to bait chamber 440 (in this embodiment, the uppermost of slots 419), bait container 400 traps air to prevent water from rising inside body 402 to a degree that it will enter into bait chamber 440 given the airtight boundary provided by body 402 down to this external point of entry. While water may pass partially into polyurethane foam seal 450, air pressure in bait chamber 440 resists passage of water through seal 450 and into bait chamber 440. In this embodiment, the uppermost of side openings 419 is spaced apart from lower boundary 478 of bait chamber by distance H to provide adequate separation between bait chamber 440 and uppermost side opening 419 to reduce the chances of water reaching bait chamber 440 positioned above the highest side opening 419 under a desired range of environmental conditions. In one preferred form, distance H is about 1 centimeter (cm). In a more preferred form, distance H is about 2.5 cm (1 inch). In another embodiment, side openings 419 are absent and with the only opening into chamber 445 being at lower end 406, the entire height of chamber 445 can operate to separate bait chamber 440 from water after polyurethane foam seal 450 is breached.

In an alternate manner of making bait container 400, polyurethane foam seal 450 is made as a separate component having a desired shape and size, such as, for example, by forming polyurethane foam seal 450 to shape in a mold or by cutting polyurethane foam seal 450 from a larger polyurethane foam workpiece, and then inserting polyurethane foam seal 450 into chamber 445 through lower end 406. In this embodiment, barrier 430 can be included or omitted.

Figure 15:
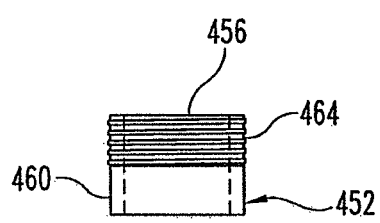
FIG. 15 is a side view of a fitting that can optionally be used with a modified version of the bait container depicted in FIG. 12.
Figure 16:
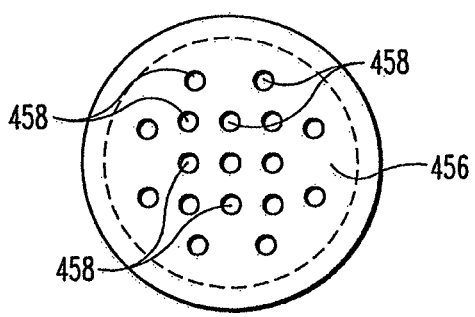
FIG. 16 is a top plan view of the fitting shown in FIG. 15.

In an alternative embodiment, barrier 430 can be held in place by fitting 452 depicted in FIGS. 15 and 16. Fitting 452 has a cylindrical form that includes sidewalls 460 upper wall 456 (also referred to as "partition 456"), and defines a chamber 462 therein. Partition 456 defines a number of openings 458 therethrough. Partition 456 can be an integral portion of fitting 452, or can be a separate part that is attached to sidewalls 460. For example, partition 456 can be in the form of a mesh screen attached to sidewalls 460. In one embodiment, partition 456 is formed from a 7 Mesh plastic canvas available from Uniek, Inc. of Waunakee, Wis. and attached to sidewalls 460 with an adhesive. In an embodiment that includes fitting 452, lower end portion 406 of body 402 of bait container 400 defines interior helical threading (not shown) about opening 416, and fitting 452 includes exterior threading 464 to engage interior threading (not shown) of lower end portion 406. When threaded through opening 416, fitting 452 holds barrier 430 in place. With barrier 430 and fitting 452 in place, polyurethane foam can be positioned in chamber 462 of fitting 452 to provide a water resistant seal for lower end portion 406. For the sake of clarity, fitting 452 is omitted from FIGS. 12, 13 and 14; however, it is to be understood that fitting 452 can optionally be included in bait container 400 as described above.

To make a bait container 400 that includes fitting 452, bait 229 is loaded into bait chamber 440 through lower opening 416, barrier 430 is placed through opening 416 to engage lower seat 420, and fitting 452 is then threaded into opening 406 to capture barrier 430. Polyurethane foam seal 450 is then positioned in chamber 462 of fitting 452 as described herein, i.e., by allowing the polyurethane foam seal 450 to cure in chamber 462 or by inserting a pre-made polyurethane foam seal 450 in chamber 462. So assembled, bait container 400 includes body 402, closure 90, barrier 430, fitting 452 and polyurethane foam seal 450.

In use of an embodiment that includes fitting 452, as barrier 430 is removed and dispersed by termites, it should be appreciated that partition 456 of fitting 452 is structured to define lowermost boundary 478b of bait 229 in bait chamber 440. As a part of fitting 452, partition 456 is comprised of a material not readily removed or altered by termites. Thus, while some smaller portions of bait 229 might drop through openings 458, the larger pieces of bait 227 are maintained by partition 456 in an upwardly offset position within body 402 of container 400 relative to terminus 402b.

A pest control device that omits sensing assembly 119 can be made in a manner similar to that described above, i.e., by affixing closure 90 to upper portion 404 of body 402, introducing bait material through lower opening 416, placing barrier 430 against lower seat 420, and then introducing a mixture of polyurethane foam precursors into chamber 445 for curing. Alternatively, in an embodiment that omits sensing assembly 119, it is possible to introduce a bait material into space 410 through upper opening 414. Such an embodiment can be made by first forming polyurethane foam seal in chamber 445 and subsequently introducing the bait material into chamber 410 through upper opening 414, followed by affixing closure 90 to upper portion 404 of body 402. In this embodiment, barrier 430 can be included or omitted. If barrier 430 is included, the polyurethane foam seal can be made in the same manner described above, that is, by inverting tube 402, positioning barrier 430 against lower seat 420, and pouring a mixture of polyurethane foam precursors into chamber 445 for curing. Alternatively, polyurethane foam seal can be made by introducing a mixture of polyurethane foam precursors into chamber 445 through upper end opening 414. For example, lower opening 416 can first be blocked by placing a temporary closure over opening 416, such as, for example, by placing a cap or other covering over lower opening 416 or by contacting lower end portion 406 against a surface such that lower opening 416 is blocked. With opening 416 blocked, a mixture of polyurethane foam precursors can be poured into chamber 445 through upper opening 414. As the mixture cures, it provides polyurethane foam seal 450 in chamber 445. In one embodiment, seal 450 is held in chamber 445 by friction after removing the temporary closure. In another embodiment, the walls of chamber 445 can be pretreated before the mixture is introduced into chamber 445 to increase adherence of seal 450 to the walls of chamber 445. In still another embodiment, the walls of chamber 445 can include surface features (not shown) such as, for example, grooves or protuberances, to increase the friction between the walls and seal 450 or to otherwise lock seal 450 in chamber 445. After polyurethane seal 450 is cured, barrier 430 can be passed through upper opening 414 and positioned in contact with seat 420, if present, or in contact with polyurethane seal 450 of seat 420 is absent, thereby separating bait chamber 440 from chamber 445. In this embodiment, seat 420 can be present or absent. If seat 420 is present, barrier 430 can be positioned against the upper surface of seat 420 rather than the lower surface of seat 420 as would occur if barrier 430 is loaded into interior space 410 through lower opening 416. In alternate embodiments, polyurethane foam seal 450 can be separately formed to shape and then inserted into chamber 445. In such embodiments, barrier 430 can be present or absent.

As will be appreciated by a person of ordinary skill in the art in view of the above, the present application provides in one aspect a bait container that defines a lower entry point for access by the targeted pests and a chamber (also referred to herein as polyurethane foam containing chamber 445) to hold a polyurethane foam barrier between this entry point and bait positioned above it. The bait container includes a first chamber for containing the bait, an upper end portion defining an upper opening into the chamber, a closure to selectively access and sealingly close the upper opening, a water-impervious side wall and a lower end portion defining a bottom terminus of the bait container and a second chamber below at least a portion of the bait. The second chamber is configured to receive and retain the polyurethane foam to reduce intrusion of water through the lower end portion when the bait container is installed in a selected orientation at least partially below ground.

As will be appreciated by a person of ordinary skill in the art, a wide variety of alterations to bait container 400 can be made. For example, in alternative embodiments, polyurethane foam chamber 445 can take on a number of different shapes and configurations, including any type of fluid communication pathway that separates bait chamber 440 from the environment of bait container 400. In alternate embodiments, chamber 445 can also be positioned at locations other than below bait chamber 440. In addition, the dimensions and proportions of body 402 can be adjusted to accommodate a wide variety of termite control devices. In addition, the contents of interior space 410 can be altered. For example, pellets 229 can be substituted with other bait materials, or can be omitted, in which case chamber 440 can be filled with polyurethane foam. For example, the bait included in chamber 440 may be composed of a composite bait material as described hereinabove, may be differently composed to target to a different pest type, may include more or fewer cellulosic food material pieces, may include a single food material piece such as a wood or synthetically formed cellulose block, may include no cellulosic food material pieces, may include an attractant with or without pesticide, and/or may be otherwise differently constituted. In addition, the polyurethane foam can be formulated to include an enhancer entrained therein, such as, for example, a cellulose powder or a sugar.

A variety of alternative bait containers and bait materials that include a polyurethane foam can be used in other embodiments as stand alone pest control devices or can be used in place of bait container 200 in pest control device 110. For example, bait material 1 described above and depicted in FIG. 1 or bait material 4 described above and depicted in FIG. 2 can be sized and shaped for placement in housing 170 in place of bait container 200 or 400. In the case of bait materials 1 and 4, such bait materials can include a pesticide material or, alternatively, a pesticide material can be absent from the bait material. If a pesticide is absent, bait material 1 or bait material 4 can operate to attract termites and establish termite feeding patterns for visual monitoring for possible later administration of a pesticide. If a pesticide is present, bait material 1 or bait material 4 can be positioned in housing 170 to serve both purposes of attracting termites and of delivering a pesticide once termites tunnel into 170 and begin feeding on bait material 1, 4. The presence of polyurethane foam matrix 3 in bait material 1 and polyurethane foam coating 6 in bait material 4, provides a barrier that prevents cellulosic food material 2 and 5, respectively, from becoming damp, thereby allowing the bait material to remain positioned in housing 170 for an extended period of time without becoming fouled.

Figure 17:
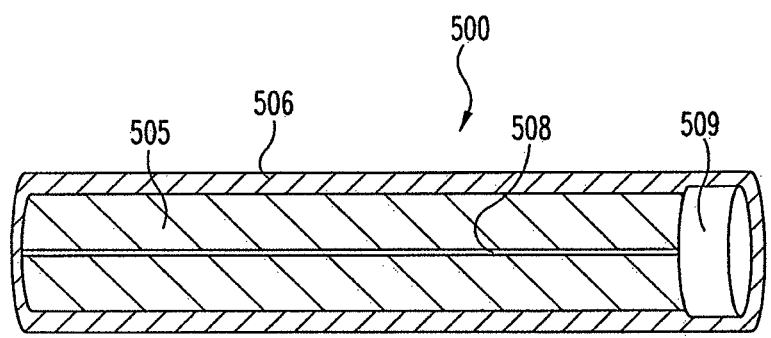
FIG. 17 is a partially sectional perspective view of another embodiment of a pest monitoring device that can be used as a stand alone pest monitoring device or as one of the pest control devices in the pest control system depicted in FIG. 3, including the pest monitoring assembly of FIG. 5.
Figure 18:
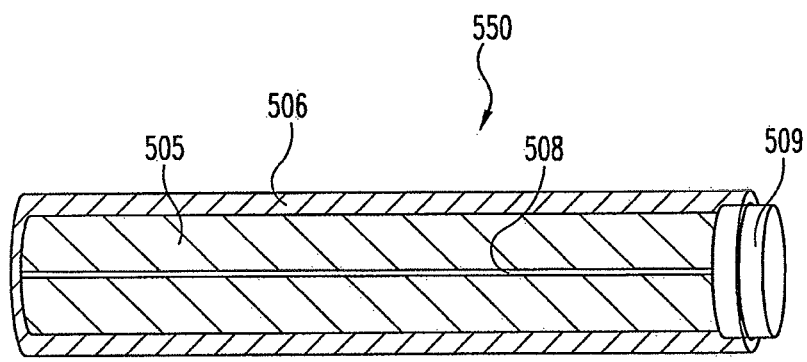
FIG. 18 is a partially sectional perspective view of yet another embodiment of a pest monitoring device that can be used as a stand alone pest monitoring device or as one of the pest control devices in the pest control system depicted in FIG. 3, including the pest monitoring assembly of FIG. 5.

Bait container 200 can alternatively be replaced by monitoring device 500 or monitoring device 550 depicted in FIGS. 17 and 18, respectively. Monitoring devices 500, 550 are similar to bait material 4 depicted in FIG. 2, but are formed to include a pest monitoring assembly including sensor subassembly 508 positioned within cellulosic food material member 505, such as, for example and without limitation, an extruded cellulosic food material, a piece of wood, a termite-edible material for an ESP monitor or a termite-edible material for a Halo monitoring device. Communication circuit subassembly 509 is operably connected to sensor subassembly 508. This pest monitoring assembly can be configured similarly to pest monitoring assembly 112 depicted in FIGS. 5-8 or can be configured in other ways as would be contemplated by a person of ordinary skill in the art. Communication circuit subassembly 509 can include electronic components inside a housing. As with bait material 4 depicted in FIG. 2, bait material 505 depicted in FIGS. 17 and 18 can optionally include a pesticide. In an alternative embodiment, food material member 505 can be replaced with polyurethane foam, which can optionally include an enhancer entrained therein, as described above.

In the embodiment depicted in FIG. 17, polyurethane foam coating 506 provides a uniform barrier around bait material member 505 and communication circuit subassembly 509. In this configuration, polyurethane foam coating provides a water resistant layer in contact with bait material member 505 that prevents moisture from the environment from contacting bait material member 505 or communication circuit subassembly 509. In one manner of making monitoring device 500 in which member 505 comprises an extruded cellulosic food material, cellulosic food material member 505 is extruded with sensor subassembly 508 therein. Communication circuit subassembly 509 is then operably connected to sensor subassembly 508, and communication circuit subassembly 509 is affixed to cellulosic food material member 505, for example, by being adhered to member 505. With cellulosic food material member 505, sensor subassembly 508 and communication circuit subassembly 509 assembled as described, polyurethane foam coating 506 is applied over cellulosic food material member 505 and communication circuit subassembly 509 to provide monitoring device 500. Communication circuit subassembly 509 is one that is operable to transmit a signal to a remote device, such as a portable interrogator 30 depicted in FIG. 3.

In the embodiment depicted in FIG. 18, polyurethane foam coating 506 provides a barrier around bait material member 505, but does not extend completely around communication circuit subassembly 509. In this embodiment, polyurethane foam coating 506 is adhered to communication circuit subassembly 509 such that polyurethane foam coating 506 and communication circuit subassembly 509 operate together to provide a water resistant barrier between bait material member 505 and its environment. With cellulosic food material member 505, sensor subassembly 508 and communication circuit subassembly 509 assembled, polyurethane foam coating 506 is applied over cellulosic food material member 505 and over a portion of communication circuit subassembly 509 to provide monitoring device 550. In one embodiment, the portion of polyurethane foam coating 506 in contact with communication circuit subassembly 509 is adhered to communication circuit subassembly to provide a water tight seal therebetween. In another embodiment, a sealing tape (not shown) can be applied over the junction of polyurethane foam coating 506 and communication circuit subassembly 509. In yet another embodiment, a cap (not shown) can be positioned over communication circuit subassembly 509 and adhered to polyurethane foam coating 506 to provide a water tight seal. In alternatively embodiments, sensor subassembly 508 and communication circuit subassembly 509 can be omitted, and the resulting devices can be used as monitors useful to indicate termite presence by visual inspection.

Figure 19:
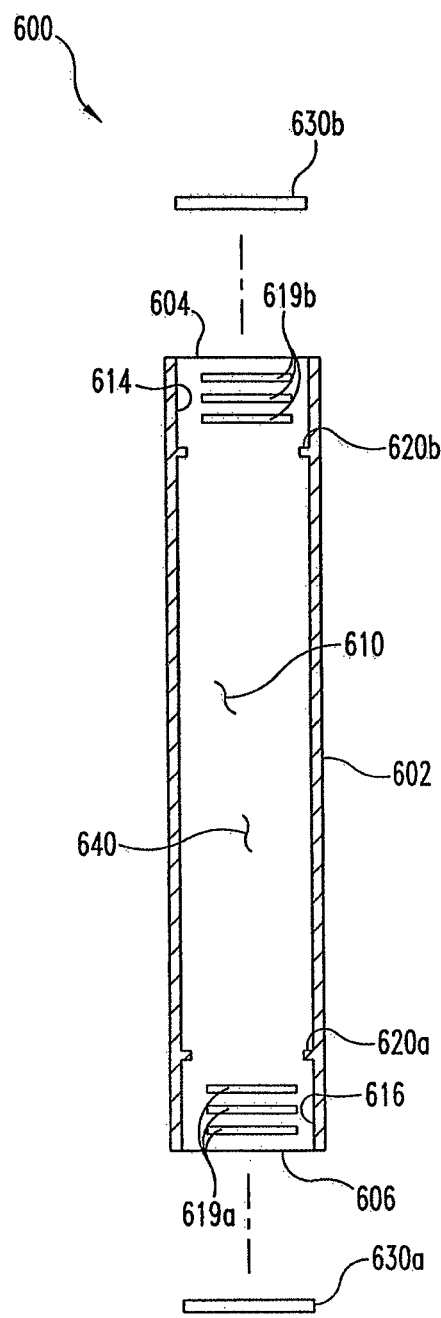
FIG. 19 depicts another embodiment bait container that can be used in a pest control device or as a stand alone bait.

In another embodiment, depicted in FIG. 19, bait container 600 has a lower end 606 configured similar to lower end 406 of bait container 400 depicted in FIG. 12, and has an upper end 604 that is configured in a similar manner. More specifically, bait container 600 includes barrier member 630a shaped and sized to fit in interior space 610 through lower opening 616 to engage lower seat 620a and barrier member 630b shaped and sized to fit in interior space 610 through upper opening 614 to engage upper seat 620b. Barriers 630a and 630b divide interior space 610 of body 602 into three sections. Barrier 630a defines a lower boundary of bait containing chamber 640 in body 602, and barrier 630b defines an upper boundary of bait containing chamber 640. Each of barriers 630a, 630b are held in place by a polyurethane foam seal (not shown) in a similar manner to polyurethane foam seal 450 described in connection with FIG. 12. Bait container 600 can also optionally include a pest monitoring assembly effective to transmit a wireless signal, as described hereinabove.

In yet another aspect of the present application, a housing, such as, for example, housing 170 depicted in FIGS. 9 and 13, can itself be filled with a composite bait material and thereby can operate as a self contained bait container. For example, to provide a composite bait material in housing 170, cellulosic food material pieces are loaded into interior space 172 through access end portion 171a to at least partially fill housing 170. After loading cellulosic food material pieces into interior space 172, a mixture of uncured polyurethane precursors is then introduced into interior space 172 of housing 170 and allowed to flow into the void space created by food material pieces and housing 170. The uncured polyurethane precursors can be introduced into interior space 172 by pouring through access end portion 171a. Alternatively, a polyurethane foam precursors can be provided in a delivery system that includes a blowing agent, such as for example, the GREAT STUFF™ polyurethane foam system that is commercially available from The Dow Chemical Company. As the mixture of precursors cures to form a polyurethane foam matrix, it expands to fill additional portions of the void space in interior space 172, and thereby substantially fill the void space. In an alternative embodiment, cellulosic food material pieces can be omitted, in which case interior space 172 is filled with polyurethane foam, which can optionally include one or more enhancers entrained therein, as described above.

To prevent the mixture of polyurethane foam precursors or the polyurethane foam as it cures from escaping housing 170 through passages 174, passages 174 can be covered before introducing the precursors into housing 170, for example, by applying a plastic film, such as, for example, shrink wrap, over the sides of housing 170. In one embodiment, the plastic film is a tape having an adhesive on one side to attach the tape to the outside surface of housing 170. After the polyurethane foam has cured, and before housing 170 with composite bait material therein is put to use, the plastic film is removed to expose passages 174 and the polyurethane foam. When an adhesive tape is used to cover passages 174, removal of the tape can operate to roughen the exposed surface of the polyurethane foam, which can increase the acceptance of the composite bait material to termites in the field. In one embodiment, housing 170 also defines a small vent hole (not shown) to allow air to escape as the polyurethane foam cures, thereby equilibrating pressure in housing 170 as the polyurethane foam cures. With reference to FIGS. 9 and 10, after the polyurethane foam is cured, removable cap 180 can be affixed to housing 170, and housing can then be installed in the ground G as shown, for example, in FIG. 4.

As will be appreciated by a person of ordinary skill in the art, a variety of additional variations and embodiments are contemplated by the present application. For example, additional examples and disclosure of different sensor types, sensor communication techniques, bait material, pesticide, and pest control devices that can be used with any of bait container embodiments described herein may be found in U.S. Pat. Nos. 6,724,312; 7,212,112; and 7,212,129; 7,348,890; and 7,262,702, all of which are incorporated by reference herein each in its entirety.

Bait containers according to any of the variations described herein can be installed in different environments, such as at above-ground locations. For above-ground bait containers, bait fouling from extended exposure to environmental moisture is not typically a problem; however, other unique challenges arise. For example, it is generally accepted that cellulosic termite food materials in above-ground bait stations should be moistened in order to attract termites for delivery of pesticides. Cellulosic material in an above-ground bait station, however, tends to become dried out after a relatively short period of time unless it is wetted and then sealed in an air tight envelope or other enclosure, which has the disadvantage of reducing the attractiveness of the bait to termites. In addition, currently available above-ground pest control devices utilize preferred texture cellulose (PTC) bait materials, which are contained in a polyethylene bag that is cut open for termite entry. When termites feed on the PTC in the bag, they also typically impart significant damage to the bag so that the PTC spills from the above-ground station when it is opened, causing a significant mess and inconvenience for users. In another aspect of the present application, there are provided termite baits adapted for above-ground use and above-ground termite control devices that are effective to hold moisture in contact with cellulosic food material over longer periods of time and/or to maintain structural integrity after termite feeding begins.

Figure 20:
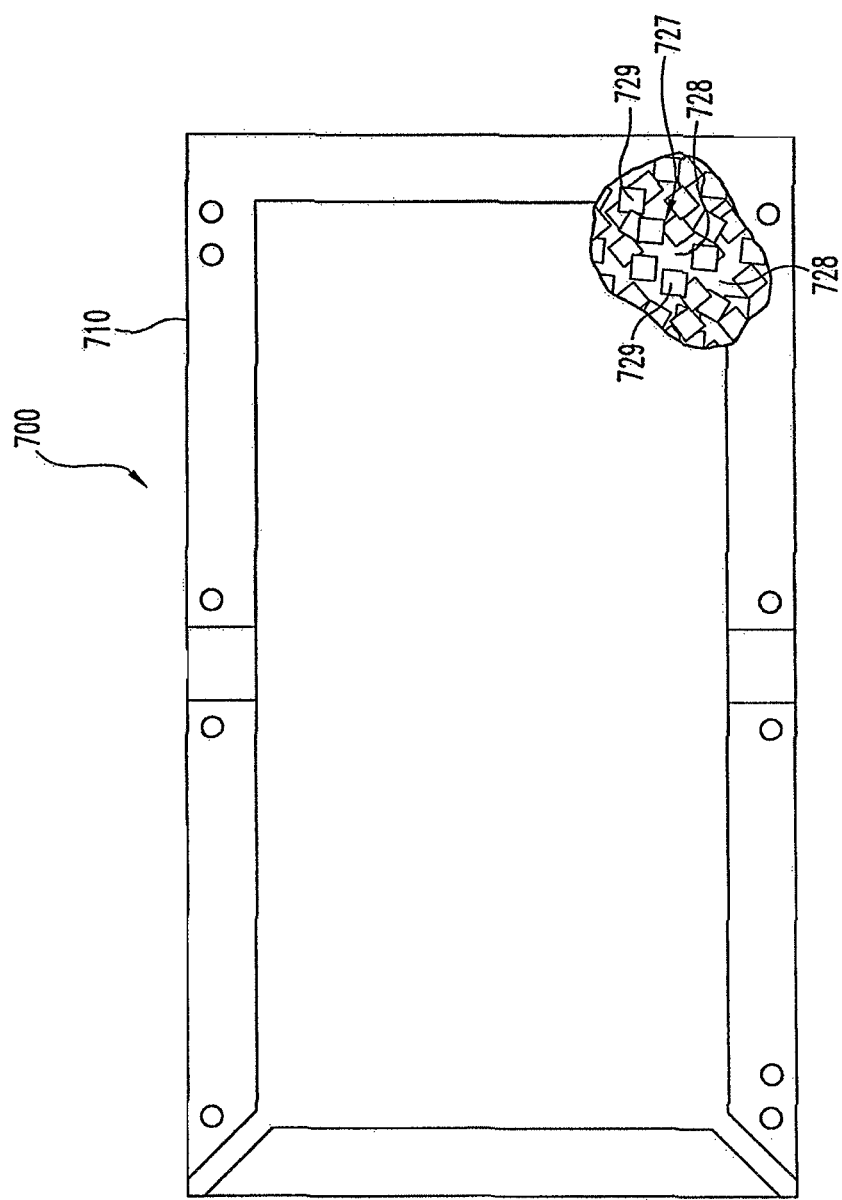
FIG. 20 depicts an above-ground bait station that includes a composite bait material therein.

With reference to FIG. 20, above-ground termite control device 700 includes housing 710 that defines an interior space and holds composite bait material 727 therein. Composite bait material 727 includes a plurality of cellulosic food material pieces 729 that are palatable to the termite species, embedded within a termite-edible or termite-displaceable polyurethane foam matrix 728. In one embodiment, the cellulosic food material pieces are cellulose briquettes, such as, for example, RECRUIT IV™ cellulose briquettes, which are commercially available from Dow Agrosciences LLC (Indianapolis, Ind.), or other cellulose briquettes, with or without a pesticide contained therein. Alternatively, cellulosic food material pieces 729 can be composed of a particulate cellulosic material or other cellulosic material as described hereinabove, with or without a pesticide contained therein. In one embodiment, foam matrix 728 is composed of a water-absorbant, open-cell polyurethane foam. In this embodiment, foam matrix 728 provides a water-absorbent scaffold surrounding most or all of cellulosic food material pieces 729 that operates to hold moisture in contact with food material pieces 729. In another embodiment, foam matrix 728 is composed of a closed-cell polyurethane foam that operates to hold moisture in contact with food material pieces 729.

A bait material of this embodiment is useful in situations where it is desirable for food material pieces 729 to be kept in a moistened state for an extended period of time, such as, for example, for use in an above-ground termite control station. While bait material 727 can eventually become dried out if it remains in a moisture free environment for a long period of time, particularly if the bait is in a hot, dry environment for an extended period of time, polyurethane foam matrix 728 is effective to significantly lengthen the amount of time for food material pieces to become dried in a given environment without being sealed in a water-impervious envelope or other container.

As will be appreciated by person skilled in the art in view of the above, in one aspect the present application provides a composite bait material operable to be consumed or displaced by one or more species of termites, the composite bait material comprising a plurality of cellulosic food material pieces that are palatable to said termite species embedded within a matrix comprising a termite-edible or termite-displaceable polyurethane foam.

In various alternative embodiments, the polyurethane foam comprises a closed-cell polyurethane foam; the matrix provides a water resistant barrier surrounding at least one of said cellulosic food material pieces; the cellulosic food material pieces comprise a food material selected from the group consisting of wood fibers, wood, purified cellulose, microcrystalline cellulose and modified polymeric cellulose; the bait material further comprises a pesticide contained within the composite bait material that is toxic to said one or more species of termite; the pesticide is selected from an immediate action pesticide and a delayed action pesticide; the pesticide comprises a member selected from the group consisting of hexaflumuron, noviflumuron, chlorpyrifos, spinosad, imidacloprid, fipronil, lufenuron, diflubenzuron, flufenoxuron, hydramethylnon and sulfuramid; the composite material is a monitor or bait for a termite control device; said composite bait material is contained within a bait enclosure; said bait enclosure is adapted to removably fit within a durable, rigid station housing; said composite bait material is contained within a monitor enclosure, said monitor enclosure further comprises one or more monitoring components for signaling termite feeding activity; the polyurethane foam comprises an enhancer entrained therein; the enhancer comprises a food material enhancer; the food material enhancer comprises a member selected from the group consisting of a particulate cellulosic material and a sugar; the food material comprises an alpha-cellulose powder; the food material enhancer comprises a particulate cellulosic material present in the polyurethane foam in an amount of up to about 95 parts per 100 parts polyurethane foam; the particulate cellulosic material is present in the polyurethane foam in an amount of from about 1 to about 75 parts per 100 parts polyurethane foam; the particulate cellulosic material is present in the polyurethane foam in an amount of from about 1 to about 45 parts per 100 parts polyurethane foam; the particulate cellulosic material is present in the polyurethane foam in an amount of from about 5 to about 30 parts per 100 parts polyurethane foam; the particulate cellulosic material is present in the polyurethane foam in an amount of from about 5 to about 25 parts per 100 parts polyurethane foam; and/or the particulate cellulosic material is present in the polyurethane foam in an amount of from about 5 to about 20 parts per 100 parts polyurethane foam.

One inventive method of the present application is a method for making a moisture-resistant composite bait material that includes providing a plurality of pieces of a cellulosic food material that is palatable to at least one species of termites in a bait enclosure, wherein the bait enclosure and the plurality of cellulosic food material pieces define a void space therebetween; introducing an uncured mixture of polyurethane foam precursors into said bait enclosure such that said mixture enters at least some of the void space; and allowing said mixture to cure to provide polyurethane foam matrix surrounding at least one of the plurality of said cellulosic food material pieces.

In various alternative embodiments, the polyurethane foam matrix is water resistant; said introducing comprises injecting the mixture into the bait enclosure; a blowing agent is used to inject the mixture into the bait enclosure; said introducing comprises pouring the mixture into the bait enclosure; said cellulosic food material comprises a food material selected from the group consisting of wood fibers, wood, purified cellulose, microcrystalline cellulose and modified polymeric cellulose; said composite bait material further comprises a pesticide that is toxic to the one or more species of termite; the pesticide is selected from an immediate action pesticide and a delayed action pesticide; the pesticide comprises a member selected from the group consisting of hexaflumuron, noviflumuron, chlorpyrifos, spinosad, imidacloprid, fipronil, lufenuron, diflubenzuron, flufenoxuron and hydramethylnon; the polyurethane foam matrix comprises an enhancer entrained therein; the enhancer comprises a particulate cellulosic material; and/or the particulate cellulosic material is present in the polyurethane foam matrix in an amount of up to about 95 parts per 100 parts polyurethane foam.

In another aspect, the present application provides a moisture-resistant composite bait material operable to be consumed or displaced by one or more species of termites, the composite bait material comprising a cellulosic food material member that is palatable to said termite species encapsulated within a termite-edible or termite-displaceable water resistant polyurethane foam coating.

In various alternative embodiments, the cellulosic food material member is selected from the group consisting of an extruded cellulosic food material, a piece of wood, a termite-edible material for an ESP monitor and a termite-edible material for a Halo monitoring device; said polyurethane foam coating comprises a closed-cell polyurethane foam; said foam coating provides a water resistant barrier between said cellulosic food material member and its environment; said coating is in contact with said food material member; said cellulosic food material member comprises a food material selected from the group consisting of wood fibers, wood, purified cellulose, microcrystalline cellulose and modified polymeric cellulose; the bait material further comprises a pesticide contained within the composite bait material that is toxic to the one or more species of termite; the pesticide is selected from an immediate action pesticide and a delayed action pesticide; the pesticide comprises a member selected from the group consisting of hexaflumuron, noviflumuron, chlorpyrifos, spinosad, imidacloprid, fipronil, lufenuron, diflubenzuron, flufenoxuron and hydramethylnon; said composite bait material member is adapted to removably fit within a durable, rigid station housing; at least one monitoring component for signaling termite feeding activity is embedded in said bait material; the polyurethane foam coating comprises an enhancer entrained therein; the enhancer comprises a particulate cellulosic material; and/or the particulate cellulosic material is present in the polyurethane foam coating in an amount of up to about 95 parts per 100 parts polyurethane foam.

Another inventive method of the present application is a method for making a moisture-resistant composite bait material that includes providing a cellulosic food material member that is palatable to at least one species of termites; and covering the cellulosic food material member with a coating comprising a polyurethane foam such that said coating provides a water resistant barrier between said cellulosic food material member and its environment.

In various alternative embodiments, the cellulosic food material member is selected from the group consisting of an extruded cellulosic food material, a piece of wood, a termite-edible material for an ESP monitor and a termite-edible material for a Halo monitoring device; said cellulosic food material member comprises a food material selected from the group consisting of wood fibers, wood, purified cellulose, microcrystalline cellulose and modified polymeric cellulose; said composite bait material further comprises a pesticide that is toxic to the one or more species of termite; the pesticide is selected from an immediate action pesticide and a delayed action pesticide; the pesticide comprises a member selected from the group consisting of hexaflumuron, noviflumuron, chlorpyrifos, spinosad, imidacloprid, fipronil, lufenuron, diflubenzuron, flufenoxuron and hydramethylnon; the polyurethane foam comprises an enhancer entrained therein; the enhancer comprises a particulate cellulosic material; and/or the particulate cellulosic material is present in the polyurethane foam in an amount of up to about 95 parts per 100 parts polyurethane foam.

In yet another aspect, the present application provides a moisture-resistant termite control device that includes a bait operable to be consumed or displaced by one or more species of termite; and a termite-edible or termite-displaceable water resistant polyurethane foam positioned to separate said bait from its environment; wherein, when said device is exposed to environmental moisture, said foam is operable to provide a moisture resistant barrier between said bait and said environmental moisture.

In one embodiment, said bait and said foam compose a composite bait material that is operable to be consumed or displaced by one or more species of termite, the composite bait material comprising a plurality of cellulosic food material pieces contained within a water resistant polyurethane foam matrix. In various alternative embodiments, the termite control device further comprises a pesticide contained within the composite bait material that is toxic to one or more species of termite; the pesticide is selected from an immediate action pesticide and a delayed action pesticide; the pesticide comprises a member selected from the group consisting of hexaflumuron, noviflumuron, chlorpyrifos, spinosad, imidacloprid, fipronil, lufenuron, diflubenzuron, flufenoxuron and hydramethylnon; the cellulosic food material comprises a member selected from the group consisting of wood fibers, wood, purified cellulose, microcrystalline cellulose and modified polymeric cellulose; the polyurethane foam matrix comprises an enhancer entrained therein; the enhancer comprises a particulate cellulosic material; the particulate cellulosic material is present in the polyurethane foam matrix in an amount of up to about 95 parts per 100 parts polyurethane foam; the termite control device further comprises a termite sensing circuit; the device further comprises a container at least partially enclosing said composite bait material, said container defining a chamber for containing the termite bait, and defining apertures for allowing termites to enter said chamber and access said composite bait material; said container includes an upper end portion defining an upper opening into the chamber, and a closure to selectively access and close the upper opening; the device further comprises a termite sensor positioned in the chamber; the termite sensor includes a circuit housing accessible through the upper opening when the closure is open and a sensing substrate downwardly extending from the circuit housing in the chamber; and/or the device further comprises a housing structured for at least partial in-ground installation, the housing terminating at a lower housing end portion located below ground level after the in-ground installation and defining an upper access opening into an interior passage to receive the bait container with the lower end portion passing through the upper access opening before the upper end portion to provide the selected orientation thereof.

In another embodiment, said bait comprises a cellulosic food material member that is palatable to said termite species and wherein said polyurethane foam comprises a water resistant coating over said food material member that separates said food material member from the device's environment. In various alternative embodiments, the termite control device further comprises a termite sensor positioned within said food material member; the termite sensor includes a circuit housing affixed to said food material member and a sensing substrate extending through said food material member from the circuit housing; said food material member has a generally tubular shape defining first and second ends; wherein said circuit housing is affixed to a first end of said food material member; and wherein said sensing substrate extends through said food material member toward said second end; said polyurethane foam coating covers said food material member and said circuit housing, thereby separating said food material member and said circuit housing from said device's environment; said polyurethane foam coating covers said food material member but does not cover said circuit housing; said polyurethane foam coating is adhered to said circuit housing and said coating and said circuit housing provide a water resistant cover separating said food material member from the device's environment; the termite control device further comprises an end cap configured to be fitted over said circuit housing and to sealingly engage said foam coating and said coating and said end cap provide a water resistant cover separating said food material member from the device's environment; the device further comprises a housing structured for at least partial in-ground installation, the housing terminating at a lower housing end portion located below ground level after the in-ground installation and defining an upper access opening into an interior passage to receive the bait; the polyurethane foam matrix comprises an enhancer entrained therein; the enhancer comprises a particulate cellulosic material; and/or the particulate cellulosic material is present in the polyurethane foam matrix in an amount of up to about 95 parts per 100 parts polyurethane foam.

In yet another embodiment, the termite control device further comprises a bait container that includes a first chamber for containing the bait, an upper end portion defining an upper opening into the first chamber, a closure to selectively access and sealingly close the upper opening, a water resistant side wall and a lower end portion defining a bottom terminus of the bait container and a second chamber below at least a portion of the bait, the second chamber configured to receive and retain the polyurethane foam to reduce intrusion of water through the lower end portion when the bait container is installed in a selected orientation at least partially below ground. In various alternative embodiments, a lowermost boundary of the bait is offset from the bottom terminus by at least one centimeter; a lowermost boundary of the bait is offset from the bottom terminus by at least one inch; the bait container includes a tubular body defining a lower opening opposite the upper opening and the device includes a termite-passable barrier separating the chamber into first bait-containing chamber and said second foam-containing chamber; the barrier is positioned between the polyurethane foam and the bait and is configured to allow termite access to the first bait-containing chamber after displacement of a portion of the polyurethane foam in the second foam-containing chamber, and the foam initially closes off the second foam-containing chamber to define an initial water resistant seal and is structured to allow the termites to form one or more passages through the foam to reach the first chamber; the barrier is composed of a material that is edible or displaceable by the termites; said closure includes a handle protrusion structured to manually move the bait container; said closure is in the form of a cap threaded to the container to resealably close the upper opening; the polyurethane foam matrix comprises an enhancer entrained therein; the enhancer comprises a particulate cellulosic material; the particulate cellulosic material is present in the polyurethane foam matrix in an amount of up to about 95 parts per 100 parts polyurethane foam; the device further comprises a termite sensor positioned in the first chamber; the termite sensor includes a circuit housing accessible through the upper opening when the closure is open and a sensing substrate downwardly extending from the circuit housing in the first chamber; the bait includes a pesticide toxic to termites; the device further comprises a housing defining an internal passage to receive the bait container therein; and/or the housing is structured for at least partial in-ground installation, the housing terminating at a lower housing end portion located below ground level after the in-ground installation and defining an upper access opening into the interior passage to receive the bait container with the lower end portion passing through the upper access opening before the upper end portion to provide the selected orientation thereof.

Yet another inventive method of the present application is a method for making a moisture-resistant termite control device that includes providing a bait container having a body that defines an internal chamber and a first opening for passing bait materials into said chamber; inserting a plurality of pieces of a cellulosic food material that is palatable to one or more species of termites into said chamber through said opening, wherein said bait container body and said cellulosic food material pieces define void spaces therebetween; introducing an uncured mixture of polyurethane foam precursors into said chamber through said opening such that said mixture surrounds a plurality of said cellulosic food material pieces; and allowing said mixture to cure to provide a polyurethane foam matrix around said plurality of said cellulosic food material pieces.

In various alternative embodiments, the polyurethane foam matrix is water resistant; said introducing comprises injecting the mixture into the bait container; a blowing agent is used to inject the mixture into the bait container; said introducing comprises pouring the mixture into the bait container; said cellulosic food material comprises a food material selected from the group consisting of wood fibers, wood, purified cellulose, microcrystalline cellulose and modified polymeric cellulose; the polyurethane foam matrix comprises an enhancer entrained therein; the enhancer comprises a particulate cellulosic material; the particulate cellulosic material is present in the polyurethane foam matrix in an amount of up to about 95 parts per 100 parts polyurethane foam; said cellulosic food material further comprises a pesticide that is toxic to the one or more species of termite; the pesticide is selected from an immediate action pesticide and a delayed action pesticide; the pesticide comprises a member selected from the group consisting of hexaflumuron, noviflumuron, chlorpyrifos, spinosad, imidacloprid, fipronil, lufenuron, diflubenzuron, flufenoxuron and hydramethylnon; the method further includes placing a termite sensor in the chamber; the opening provides termite access to the chamber; the container body includes a second opening for one or more of inserting the cellulosic food material pieces into the chamber, introducing the polyurethane foam into the chamber or providing termite access to the chamber; the container body includes a second opening, the second opening operable as a vent to allow air to escape from the void spaces during said introducing of the mixture or as the mixture cures to provide a polyurethane foam; the bait container body is tubular and has a first end, a second end and a sidewall extending from the first end to the second end; the first opening is in the first end; the side wall defines one or more additional openings into the chamber; the method further includes, after the mixture is allowed to cure, removing excess foam from the sidewall that escapes from the chamber through the additional openings as the mixture cures; the method further includes, before said introducing, placing a cover over the additional openings in the sidewalls to prevent escape of the polyurethane foam from the chamber through the additional openings during said introducing or as the mixture cures; the cover comprises a shrink wrap cover; the cover comprises a tape having an adhesive on at least one side; the container body includes a second opening in the second end for one or more of inserting the cellulosic food material pieces into the chamber, introducing the polyurethane foam into the chamber or providing termite access to the chamber; the method further includes, before said introducing, covering said second opening to prevent escape of the polyurethane foam from the chamber through said second opening during said introducing or as the mixture cures; and/or said introducing comprises, injecting, spraying or pouring.

In yet another aspect, the present application provides an above ground termite control device that includes a housing configured to hold a composite bait material; and a composite bait material contained within said housing, the composite bait material including a plurality of cellulosic food material pieces operable to be consumed or displaced by one or more species of termite and a termite-edible or termite-displaceable polyurethane foam matrix surrounding at least some of the cellulosic food material pieces; wherein the polyurethane foam is effective to hold moisture in the channels to keep the food material pieces moist for an extended period of time.

In various alternative embodiments, the polyurethane foam comprises an open-cell polyurethane foam and defines an internal network of channels opening through pores on the surface of the polyurethane foam; the device further comprises a pesticide contained within the composite bait material that is toxic to one or more species of termite; the pesticide is selected from an immediate action pesticide and a delayed action pesticide; the pesticide comprises a member selected from the group consisting of hexaflumuron, noviflumuron, chlorpyrifos, spinosad, imidacloprid, fipronil, lufenuron, diflubenzuron, flufenoxuron and hydramethylnon; the cellulosic food material comprises a member selected from the group consisting of wood fibers, wood, purified cellulose, microcrystalline cellulose and modified polymeric cellulose; the polyurethane foam matrix comprises an enhancer entrained therein; the enhancer comprises a particulate cellulosic material; and/or the particulate cellulosic material is present in the polyurethane foam matrix in an amount of up to about 95 parts per 100 parts polyurethane foam.

Still another inventive method of the present application is a method for making an above-ground termite control device that includes providing a bait container having a body that defines an internal chamber and a first opening providing access into said chamber; inserting a plurality of pieces of a cellulosic food material that is palatable to one or more species of termites into said chamber through said opening, wherein said bait container body and said cellulosic food material pieces define void spaces therebetween; introducing an uncured mixture of polyurethane foam precursors into said chamber through said opening such that said mixture surrounds a plurality of said cellulosic food material pieces; and allowing said mixture to cure to provide a polyurethane foam matrix around said plurality of said cellulosic food material pieces.

In various alternative embodiments, the polyurethane foam matrix comprises an open-cell polyurethane foam; said introducing comprises injecting the mixture into the bait container; a blowing agent is used to inject the mixture into the bait container; said introducing comprises pouring the mixture into the bait container; said cellulosic food material comprises a food material selected from the group consisting of wood fibers, wood, purified cellulose, microcrystalline cellulose and modified polymeric cellulose; the polyurethane foam matrix comprises an enhancer entrained therein; the enhancer comprises a particulate cellulosic material; the particulate cellulosic material is present in the polyurethane foam matrix in an amount of up to about 95 parts per 100 parts polyurethane foam; said cellulosic food material further comprises a pesticide that is toxic to the one or more species of termite; the pesticide is selected from an immediate action pesticide and a delayed action pesticide; and/or the pesticide comprises a member selected from the group consisting of hexaflumuron, noviflumuron, chlorpyrifos, spinosad, imidacloprid, fipronil, lufenuron, diflubenzuron, flufenoxuron and hydramethylnon.

Reference will now be made to the following Examples, which describe laboratory work directed to selected polyurethane foam formulations. It is understood that no limitation to the scope of the application is intended thereby. The Examples are intended to be illustrative, are provided solely to promote a full understanding of the concepts embodied in the application, and are not intended to be limiting or otherwise restrictive as to the nature and scope of the inventions set forth herein.

EXAMPLES

Example One

Testing Moisture Resistance of a Composite Bait Material

To test the moisture resistance of a composite bait material including a closed cell polyurethane foam matrix, four bait tubes were made to include cellulosic food material pieces encapsulated in a closed cell polyurethane foam matrix, and the bait tubes were then soaked overnight in a red dye solution to determine the effectiveness of the polyurethane foam matrix to operate as a moisture barrier between the solution and the cellulosic food material pieces.

To make the bait tubes, PTC briquettes were poured into four bait tubes similar to bait tube 200 depicted in FIG. 8, in which openings 219 and 216 had been covered with a cellophane wrapper. A mixture of polyurethane precursors was then introduced into each tube. For this experiment, the mixture of polyurethane precursors used was the GREAT STUFF™ polyurethane foam product that is commercially available from The Dow Chemical Company. The GREAT STUFF™ product is an expanding foam product that entrains a gaseous blowing agent into the mixture as it is released from its container.

After the mixture of polyurethane foam precursors was introduced into the bait tubes and allowed to cure, the cellophane wrapper was removed and the bait tubes were submerged in a red dye solution and allowed to soak overnight.

The following day, the composite bait material in each bait tube was observed visually, and was then sectioned using a cutting blade to score the number of PTC briquettes in the composite bait material that had been stained by the dye solution versus the number of PTC briquettes that remained free from dye. The percentage of PTC briquettes in each tube that were not stained by the dye after the overnight soak test are set forth below (wherein the parenthetical ratios for each tube include a numerator identifying the number of briquettes that were not stained and a denominator identifying the total number of briquettes in the tube):

| Tube 1: | 59% (83/141) |
| Tube 2: | 83% (174/210) |
| Tube 3: | 50% (95/189) |
| Tube 4: | 70% (130/185) |

While some of the PTC briquettes in the composite bait material were stained by the red dye solution, it appears that this staining resulted from openings in the polyurethane foam matrix caused by the PTC briquettes that were positioned against the cellophane wrapping during curing of the polyurethane foam, and channels caused by PTC briquettes in contact with one another, which allowed the dye to pass from one PTC briquette to another. These results establish that the polyurethane foam matrix did provide a moisture barrier between the solution and PTC briquettes that it encapsulated.

Example Two

Manufacturing a Composite Bait Material Including a Food Material Enhancer

A series of composite bait materials were made to include polyurethane foam having alpha-cellulose powder entrained therein. To make these composite bait materials, before mixing the first polyol component with PAPI™ isocyanate, varying amounts of alpha-cellulose powder were mixed into the first polyol component. When the curing of the polyurethane foam was complete, the alpha-cellulose powder was entrained in and dispersed throughout the foam. The amounts of alpha-cellulose included in various examples where selected to produce polyurethane foams having 5 parts alpha-cellulose per 100 parts foam, 10 parts alpha-cellulose per 100 parts foam and 15 parts alpha-cellulose per 100 parts foam.

Example Three

Termite Penetration/Consumption Testing

The composite materials made as described in Example Two were tested against a polyurethane foam having 0 parts alpha-cellulose per 100 parts foam (referred to herein as the "blank foam treatment") to determine whether termites preferentially consume and/or penetrate polyurethane foam having alpha-cellulose powder entrained therein.
One-Way No-Choice Test (Consumption Test)

A one-way no-choice test was conducted to determine consumption of polyurethane foams having different levels of alpha-cellulose powder entrained therein by R. flavipes termites. Six repetitions of the standard one-way no-choice test with cups was conducted using 100 termites per repetition in Lab Conviron at 28° C. and 60% relative humidity. All samples were provided in the form of ½ inch×1 inch foam blocks and were placed in ½ cut plastic weight boats to allow termites free access to the samples. After 7 days, each foam sample was dried in an oven at 120° C. for 1 hour and placed in a dessicator for at least 2 hours. After drying, the samples were weighed to determine the level of consumption of the samples.

Visual inspection of the samples indicated that the termites were visibly feeding on each of the foam samples that included alpha-cellulose powder, but minimal consumption of the blank foam treatment was observed. It appeared that the termites were consuming the foam because there did not appear to be any foam pieces scattered about the bioassay. The results obtained after drying and weighing are provided below:

TABLE 2

Continuous Force-Feeding (No-Choice) Exposure (7 d). Feeding Response of R. flavipes to Various Polyurethane Foam Formulations Containing Various Levels of Alpha-cellulose.

| Treatment | mg consumed after 7 days (mean ± SEM)* |
|---|---|
| Polyurethane Foam with 25 parts Alpha-cellulose/100 parts foam | 7.69 ± 0.693 (a) |
| Polyurethane Foam with 10 parts Alpha-cellulose/100 parts foam | 6.06 ± 1.35 (ab) |
| Polyurethane Foam with 5 parts Alpha-cellulose/100 parts foam | 3.95 ± 0.8 (b) |
| Polyurethane Foam (blank) with 0 parts Alpha-cellulose/100 parts foam | 0.98 ± 0.31 (c) |
| Each treatment replicated 6 times (100 termites per rep). | *Within this column, means followed by same letter are not significantly different (ANOVA + LSD; p > 0.10). SEM = Standard Error of the Mean |

These results confirm that the addition of alpha-cellulose powder to the polyurethane foam increases consumption of the foam by R. Flavipes and, in general, the more alpha-cellulose added to the foam, the greater the consumption by the termites.
Forced Feeding Test (Penetration Test)

A forced feeding test was conducted in a 3-cup Gladware Bioassay unit to determine the amount of time for R. flavipes termites to penetrate the sample materials described above. Because the samples are not easily wrapped around blocks, the test samples were prepared by cutting approximately a one inch square piece of each sample (6 each) and placing each piece on a flat side of a one inch square block of MD-499, which is the aspen wood currently used in SENTRICON® Termite Stations. All remaining sides of the MD-499 block were covered with aluminum foil, securing the sample in place. The block is placed with sample side exposed only through an approximate ¾ inch×¾ inch window opening cut in the bottom center of a 60×15 mm Petri dish. Termites were allowed access to the foam samples only through the window with only the samples exposed. A weight was placed on top of each sample to keep the sample in firm contact with the MD-499 blocks. Samples were checked daily, and a record was made when termites penetrated completely through to the wood block.

After five days, the termites were observed to penetrate the foam samples containing alpha-cellulose powder by chewing and/or tunneling multiple holes through the foam samples to the wood block, usually at 2 to 4 locations. Feeding on the blank foam (i.e., polyurethane foam sample without alpha-cellulose) was significantly less than feeding on foam samples containing alpha-cellulose. Results of this test are set forth in the following table:

TABLE 3

Feeding Penetration of Various Polyurethane Foam Samples by R. Flavipes in a No-Choice Force Feeding Test.

| Treatment | % Samples Penetrated by Termites, Days Post-Infestation | | | | |
|---|---|---|---|---|---|
| | Day 1 | Day 2 | Day 3 | Day 4 | Day 5 |
| Polyurethane foam with 0 parts alpha-cellulose/100 parts foam | 0 | 16.7 | 50 | 66.7 | 83.3 |
| Polyurethane foam with 5 parts alpha-cellulose/100 parts foam | 0 | 66.7 | 83.3 | 100 | 100 |
| Polyurethane foam with 10 parts alpha-cellulose/100 parts foam | 33.3 | 83.3 | 100 | 100 | 100 |
| Polyurethane foam with 25 parts alpha-cellulose/100 parts foam | 16.7 | 66.7 | 100 | 100 | 100 |

Example Four

Manufacturing a Composite Bait Material

Another composite bait material was made by pouring cellulose pellets into a bait tube similar to bait tube 200 depicted in FIG. 8, with openings 219 and 216 covered. A mixture of polyurethane precursors was then introduced into the tube. The mixture of polyurethane precursors was made as follows:
(1) A first polyol component of a mixture of precursor ingredients for making a polyurethane foam was made by mixing the following ingredients in the identified proportions:
  (i) 50 parts VORANOL 360™ polyol available from Dow Chemical Company
  (ii) 50 parts DSD 301.01 polyol available in Europe from Dow Chemical Company
  (iii) 3 parts TEGOSTAB D-8404™ surfactant
  (iv) 0.2 parts POLYCAT 77™ catalyst
  (v) 7 parts water.

(2) The first polyol component was mixed with PAPI™ isocyanate to provide a mixture of uncured polyurethane foam precursor ingredients. Addition of the isocyanate initiated the curing reaction.

The mixture of uncured polyurethane foam precursor ingredients was then poured in the bait tube, filling void spaces between the cellulose pellets. As the curing reaction proceeded at room temperature, the mixture expanded to fill further portions of the void space. After a curing time of about 5 minutes, curing was complete.

Example Five

Termite Activity Testing

To test the termite activity of a series composite bait material over time compared to a typical wood monitor, bait tubes were made as described above in connection with the embodiment depicted in FIGS. 5-11, in which cellulosic food material pieces were encapsulated in a polyurethane foam matrix. In some bait tubes, the polyurethane foam included a food material enhancer entrained therein in varying amounts. Specifically, a series of composite bait material were made by pouring cellulose pellets into a bait tube similar to bait tube 200 depicted in FIG. 8, with openings 219 and 216 covered. The cellulose pellets did not include a pesticide, but had been soaked in a sports drink (referred to herein as "EOG"), which operates as a feeding stimulant in the pellets. Various mixtures of polyurethane precursors were then introduced into the tubes. Some of the composite bait materials were made to include polyurethane foam having different amounts of alpha-cellulose powder entrained therein. In composite bait materials including alpha-cellulose powder, when the curing of the polyurethane foam was complete, the alpha-cellulose powder was entrained in and dispersed throughout the foam. The amounts of alpha-cellulose included in various examples where selected to produce polyurethane foams having 5 parts alpha-cellulose per 100 parts foam (referred to herein as "5% alpha cellulose") and 10 parts alpha-cellulose per 100 parts foam (referred to herein as "10% alpha cellulose"). Other bait tubes were made without alpha-cellulose particles entrained in the polyurethane foam.

Bait tube housings similar to housing 170 depicted in FIGS. 9 and 10 were installed in the ground at various field sites known to have colonies of termites present. Four sites were selected, including a site in Florida having an active colony of *Reticulitermes flavipes* (hereafter, "Site 1"), a site in Florida having an active colony of *Reticulitermes hageni* (hereafter, "Site 2"), a site in Louisiana having an active colony of *Coptotermes formosanus* (hereafter, "Site 3"), and a site in Mississippi having an active colony of *Reticulitermes flavipes* (hereafter, "Site 4"). At each site, multiple replications of the test were performed. In each replication, four (4) housings were installed at locations equidistant from feeding termites, and four different bait tubes were installed in the four housings, one including a composite bait material including polyurethane foam (without alpha-cellulose entrained therein) and cellulose pellets (hereinafter "Test Material 1"), a second including a composite bait material including 5% alpha cellulose polyurethane foam and cellulose pellets (hereinafter "Test Material 2"), a third including a composite bait material including 10% alpha cellulose polyurethane foam and cellulose pellets (hereinafter "Test Material 3"), and a fourth including a conventional wood monitor, either MD-499 or southern yellow pine (hereafter "Wood Bait Material").

After installation of the bait tubes as described above, the tubes were inspected after 90 days and after 180 days for the presence of termite activity in the tubes. The percent of tubes showing activity at each site at 90 days and at 180 days are set forth in the following Tables 4 and 5, respectively:

TABLE 4

Bait activity at 90 days for trials with polyurethane foam bait tubes tested against *Reticulitermes* spp. In Mississippi and Florida and against *Coptotermes formosanus* in Louisiana

| Treatment | Percent of Tubes with Active Termites |
|---|---|
| *Reticulitermes flavipes* - Florida (Site 1) | |
| Test Material 1 | 0 |
| Test Material 2 | 0 |
| Test Material 3 | 0 |
| Wood Bait Material | 50.0 |
| *Reticulitermes hageni* - Florida (Site 2) | |
| Test Material 1 | 9.1 |
| Test Material 2 | 9.1 |
| Test Material 3 | 9.1 |
| Wood Bait Material | 18.2 |
| *Coptotermes formosanus* - Louisiana (Site 3) | |
| Test Material 1 | 75.0 |
| Test Material 2 | 75.0 |
| Test Material 3 | 81.3 |
| Wood Bait Material | 43.8 |
| *Reticulitermes flavipes* - Mississippi (Site 4) | |
| Test Material 1 | 27.3 |
| Test Material 2 | 36.4 |
| Test Material 3 | 36.4 |
| Wood Bait Material | 18.2 |

TABLE 5

Bait activity at 180 days for trials with polyurethane foam bait tubes tested against *Reticulitermes* spp. In Mississippi and Florida and against *Coptotermes formosanus* in Louisiana

| Treatment | Percent of Tubes with Active Termites |
|---|---|
| *Reticulitermes flavipes* - Florida (Site 1) | |
| Test Material 1 | 10.0 |
| Test Material 2 | 20.0 |
| Test Material 3 | 10.0 |
| Wood Bait Material | 70.0 |
| *Reticulitermes hageni* - Florida (Site 2) | |
| Test Material 1 | 27.3 |
| Test Material 2 | 27.3 |
| Test Material 3 | 45.5 |
| Wood Bait Material | 27.3 |
| *Coptotermes formosanus* - Louisiana (Site 3) | |
| Test Material 1 | 87.5 |
| Test Material 2 | 93.8 |
| Test Material 3 | 87.5 |
| Wood Bait Material | 68.8 |
| *Reticulitermes flavipes* - Mississippi (Site 4) | |
| Test Material 1 | 27.3 |
| Test Material 2 | 36.4 |
| Test Material 3 | 45.5 |
| Wood Bait Material | 36.4 |

While multiple embodiments of the invention have been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected. Any theory, mechanism of operation, proof, or finding stated herein is meant to further enhance understanding of the present application and is not intended to make the present application in any way dependent upon such theory, mechanism of operation, proof, or finding. It should be understood that any use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. An above ground termite control device, comprising: a housing configured to hold a composite bait material; and a composite bait material contained within said housing, the composite bait material including a plurality of cellulosic food material pieces operable to be consumed or displaced by one or more species of termite and a termite-edible or termite-displaceable polyurethane foam matrix surrounding at least some of the cellulosic food material pieces,
wherein the polyurethane foam provides a moisture barrier protecting the cellulosic food material pieces from becoming damp.

2. The device of claim 1 wherein the polyurethane foam comprises a rigid open-cell polyurethane foam and defines an internal network of channels opening through pores on the surface of the polyurethane foam.

3. The device of claim 1, further comprising a pesticide contained within the composite bait material that is toxic to one or more species of termite.

4. The device of claim 3 wherein the pesticide is selected from an immediate action pesticide and a delayed action pesticide.

5. The device of claim 3 wherein the pesticide comprises a member selected from the group consisting of hexaflumuron, noviflumuron, chlorpyrifos, spinosad, imidacloprid, fipronil, lufenuron, diflubenzuron, flufenoxuron and hydramethylnon.

6. The device of claim 1 wherein the cellulosic food material comprises a member selected from the group consisting of wood fibers, wood, purified cellulose, microcrystalline cellulose and modified polymeric cellulose.

7. The device of claim 1 wherein the polyurethane foam matrix comprises an enhancer entrained therein.

8. The device of claim 7 wherein the enhancer comprises a particulate cellulosic material.

9. The device claim 8 wherein the particulate cellulosic material is present in the polyurethane foam matrix in an amount of up to about 95 parts per 100 parts polyurethane foam.

10. A method for making an above-ground termite control device, comprising: providing a bait container having a body that defines an internal chamber and a first opening providing access into said chamber; inserting a plurality of pieces of a cellulosic food material that is palatable to one or more species of termites into said chamber through said opening, wherein said bait container body and said cellulosic food material pieces define void spaces therebetween; introducing an uncured mixture of polyurethane foam precursors into said chamber through said opening such that said mixture surrounds a plurality of said cellulosic food material pieces; and allowing said mixture to cure to provide a polyurethane foam matrix around said plurality of said cellulosic food material pieces,
wherein the polyurethane foam provides a moisture barrier protecting the cellulosic food material pieces from becoming damp.

11. The method of claim 10 wherein the polyurethane foam matrix comprises a rigid open-cell polyurethane foam.

12. The method of claim 10 wherein said introducing comprises injecting the mixture into the bait container.

13. The method of claim 12 wherein a blowing agent is used to inject the mixture into the bait container.

14. The method of claim 10 wherein said introducing comprises pouring the mixture into the bait container.

15. The method of claim 10 wherein said cellulosic food material comprises a food material selected from the group consisting of wood fibers, wood, purified cellulose, microcrystalline cellulose and modified polymeric cellulose.

16. The method of claim 10 wherein the polyurethane foam matrix comprises an enhancer entrained therein.

17. The method according to claim 16 wherein the enhancer comprises a particulate cellulosic material.

18. The method according to claim 17 wherein the particulate cellulosic material is present in the polyurethane foam matrix in an amount of up to about 95 parts per 100 parts polyurethane foam.

19. The method of claim 10 wherein said cellulosic food material further comprises a pesticide that is toxic to the one or more species of termite.

20. The method of claim 19 wherein the pesticide is selected from an immediate action pesticide and a delayed action pesticide.

21. The method of claim 19 wherein the pesticide comprises a member selected from the group consisting of hexaflumuron, noviflumuron, chlorpyrifos, spinosad, imidacloprid, fipronil, lufenuron, diflubenzuron, flufenoxuron and hydramethylnon.

* * * * *